(12) United States Patent
Dolan et al.

(10) Patent No.: US 12,376,826 B2
(45) Date of Patent: Aug. 5, 2025

(54) DETERMINING THE CONDITION OF VESSELS IN THE BODY

(71) Applicant: VERSONO MEDICAL LIMITED, Galway (IE)

(72) Inventors: Finbar Dolan, Galway (IE); Dion Guilfoyle, Galway (IE); Ben Kinsella, Galway (IE); Ivan Mooney, Galway (IE); Hugh O'Donoghue, Galway (IE); Mary O'Donoghue, Galway (IE); Jim Smedley, Galway (IE)

(73) Assignee: VERSONO MEDICAL LIMITED, Galway (IE)

( * ) Notice: Subject to any disclaimer, the term of this patent is extended or adjusted under 35 U.S.C. 154(b) by 237 days.

(21) Appl. No.: 18/258,082

(22) PCT Filed: Dec. 17, 2021

(86) PCT No.: PCT/EP2021/086669
§ 371 (c)(1),
(2) Date: Jun. 16, 2023

(87) PCT Pub. No.: WO2022/129623
PCT Pub. Date: Jun. 23, 2022

(65) Prior Publication Data
US 2024/0032893 A1    Feb. 1, 2024

(30) Foreign Application Priority Data
Dec. 17, 2020  (GB) ..................... 2020065

(51) Int. Cl.
*A61B 8/12*     (2006.01)
*A61B 8/00*     (2006.01)
(Continued)

(52) U.S. Cl.
CPC ............... *A61B 8/12* (2013.01); *A61B 8/085* (2013.01); *A61B 8/0891* (2013.01);
(Continued)

(58) Field of Classification Search
CPC ..................... A61B 8/12; A61B 8/446; A61B 2017/22014–22018
See application file for complete search history.

(56) References Cited

U.S. PATENT DOCUMENTS 5,284,148 A        2/1994  Dias et al.
2004/0260180 A1*  12/2004  Kanai ................... A61B 8/485
                                                    600/449
(Continued)

FOREIGN PATENT DOCUMENTS

WO    2019152898 A1    8/2019

OTHER PUBLICATIONS

International Search Report and Written Opinion in corresponding Application No. PCT/EP2021/086669, dated Mar. 22, 2022, (18 pages).

*Primary Examiner* — Colin T. Sakamoto
(74) *Attorney, Agent, or Firm* — Bookoff McAndrews, PLLC

(57) ABSTRACT

Endovascular apparatus for determining the condition of a vessel in a body comprises an elongate waveguide element such as a wire and an activation unit comprising a source of ultrasonic energy to activate the waveguide element, hence transmitting ultrasonic energy to an active distal section of the waveguide element. A signal acquisition system acquires feedback signals from the apparatus for interpretation of vessel condition. The signal acquisition system comprises at least one acoustic sensor for acquiring acoustic feedback signals generated by the apparatus when the waveguide element is activated. Data sets may be generated from (Continued)

acoustic and non-acoustic feedback signals and combinations of, or comparisons between, those data sets can characterise the condition of the vessel, including any lesion such as a blockage in the vessel.

28 Claims, 14 Drawing Sheets

(51) Int. Cl.
*A61B 8/08* (2006.01)
*A61B 17/22* (2006.01)

(52) U.S. Cl.
CPC ............ *A61B 8/4272* (2013.01); *A61B 8/445* (2013.01); *A61B 2017/22014* (2013.01)

(56) References Cited

U.S. PATENT DOCUMENTS

2017/0215837 A1* 8/2017 Ramakrishna ....... A61B 8/4472
2021/0007760 A1* 1/2021 Reisin .................... G16H 40/63

\* cited by examiner

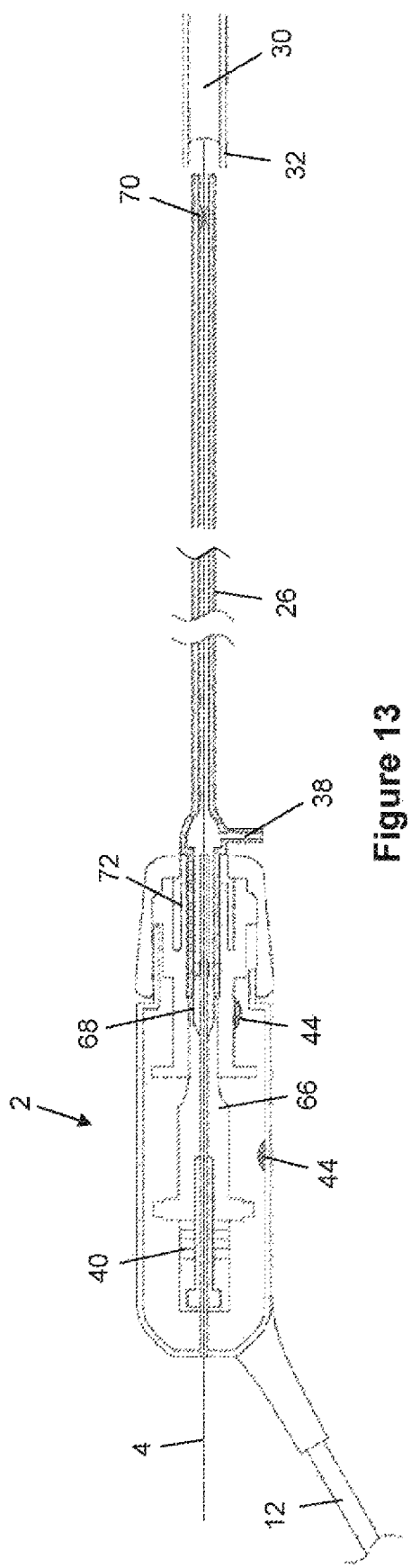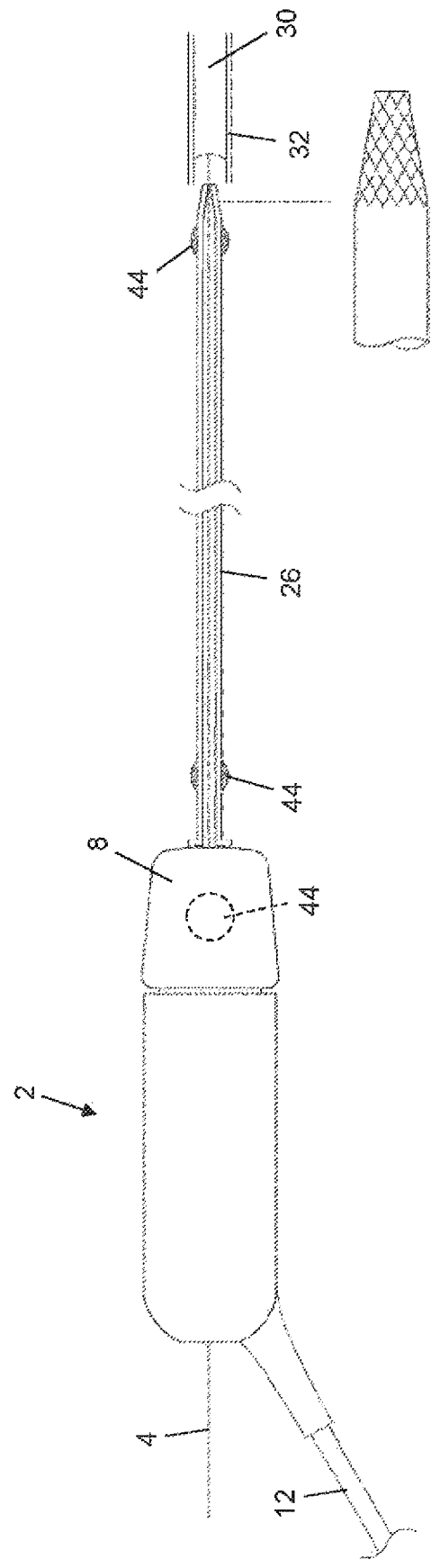

DETERMINING THE CONDITION OF VESSELS IN THE BODY

This invention relates to techniques for determining the condition of vessels in the body, including characterising blockages in such vessels. The invention is particularly concerned with elongate elements such as wires and catheters used to pass through or to cross blockages in the body, for example to treat ischaemia, such elements therefore being known in the art as crossing wires and crossing catheters.

Crossing wires will be used in this specification to exemplify the inventive concept but it should be understood that the inventive concept can also be applied to crossing catheters. It should also be understood that crossing wires and crossing catheters may have additional functions such as guiding follow-on therapies once a blockage has been crossed.

Ischaemia is an inadequate supply of blood to an organ of the body. In atherosclerotic blood vessels, ischaemia occurs as a result of the blood vessels being blocked by obstructions that arise from lesions in the vessel wall, from atherosclerotic plaque, or from emboli arising from other sources. By partially or fully occluding a blood vessel, a blockage restricts blood flowing to tissues distal to the blockage, causing cell death and a rapid deterioration in the health of those tissues.

Blockages such as chronic total occlusions (CTOs) result it an ischaemic response to wounds and trauma, leading to refractory ulceration of wounds and cuts and other insults to tissues. This anticipated response makes surgical intervention unattractive. Thus, a preferred way to treat such blockages is by minimally invasive, endovascular procedures such as angioplasties. In such procedures, small-diameter therapeutic devices are introduced into the vasculature via guidewires or catheters, navigated to the blockage via the lumen of veins and arteries and deployed at the site of the lesion to restore patency. Procedures used to revascularise occlusions in the coronary and peripheral arteries by treating chronic atherosclerotic plaques can also be used in the treatment of acute embolic occlusions, thrombi, or occlusive blood clots.

More generally, guidewires or catheters are used in other minimally-invasive procedures to introduce other devices and instruments into vessels or other cavities of the body to enable inspection, diagnosis and different types of treatment. Other medical procedures that use guidewires or catheters include gastrointestinal, urological and gynaecological procedures, all of which may require a passageway to be formed through a blockage to facilitate the passage of often larger devices to the site of lesions or other targeted tissues distal to the lesions.

In endovascular procedures, an artery is selected and recruited for use in obtaining access to the vasculature. The selection is based on the ability of the artery to accommodate the passage of the intended diagnostic or therapeutic device to the target site and the extent to which it may minimise tissue and patient trauma.

In revascularising procedures for peripheral arteries, access is often made by surgical cutdown and puncture to the femoral, popliteal and pedal arteries, commonly known in medical terms as the Seldinger technique. Once access is made, an introducer wire and an introducer sheath are inserted into the vessel and secured at the site. The sheath acts as a port for the introduction, withdrawal and exchange of devices and to minimise abrasion of the arterial tissue. Then, catheters and guidewires are introduced into the artery to provide further protection and to assist in navigating a device to the target site.

A guidewire, for example, is pushed carefully along the lumen of the vessel to avoid trauma to the vessel wall and is navigated to the site of the occlusion. In successful procedures, the guidewire is then pushed across, or through, the occlusion and is kept in situ to act as a guide over which a diagnostic or therapeutic device, such as a balloon catheter and/or a stent, is tracked to the site of the occlusion. Visualisation of the progression of guidewires, catheters and other diagnostic or therapeutic devices through the anatomy is typically done by X-ray, duplex ultrasound or MRI.

In the case of balloon angioplasty, a balloon catheter is introduced over the guidewire into the vessel and navigated to the site of the occlusion. The balloon is then dilated, pushing the occluding material outwardly to restore blood flow. Sometimes a stent is placed within the lesion to act as a scaffold to maintain patency of the vessel.

Conventional endovascular wires are of various constructions and designs to facilitate access to, and crossing of, lesions in different anatomies and to support different devices, Such wires are available in a range of outer diameters and lengths associated with the anatomies concerned and the distances over which they are expected to operate. They are made from various materials, most typically stainless steels or NiTi (Nitinol). Their manufacture typically involves cold-working the material while forming it into a wire and then machining or grinding the wire to different profiles to effect a desirable performance. As an example, specific tapers may be ground over the length of a wire to produce differential degrees of flexibility along the length of the wire.

At its distal end in particular, the wire must have sufficient flexibility to conform to the tortuosity of a vessel and yet must also have sufficient axial and torsional strength to transmit force to the distal tip and to cross through a lesion. A balance is required between flexibility expressed as 'trackability' and rigidity expressed as 'pushability' or 'steerability'. Pushability requires longitudinal, columnar stiffness whereas steerability requires torsional stiffness.

Conventional endovascular wires are operated by their proximal end being pushed, pulled and torqued to navigate to the site of a blockage and are then pushed through the blockage. Thus, they are passive, in the sense that, they do not transmit any energy other than that applied by the clinician.

The anatomies in which endovascular procedures may be conducted include, but are not limited to, the coronary, neurovascular and the peripheral arteries that service the lower limbs. Different anatomies are associated with different types of lesions. For example, lesions found in the various peripheral vessels pose different challenges to those found in the coronary arteries.

In many instances, occlusions are too challenging for conventional endovascular elements such as guidewires to cross through. In this respect, atherosclerotic plaque is composed of materials whose constitution becomes progressively stiffer over time. For example, the iliac, femoral, popliteal and infra-popliteal arteries are susceptible to extensive calcification that poses a severe impediment to successful endovascular procedures. Conventional endovascular elements are limited when trying to cross nearly- or totally-occluding blockages that may also be significantly calcified.

For example, in peripheral infra-iliac procedures, an occlusion may have a calcified proximal cap that will be encountered in a preferred antegrade or femoral approach.

Much time may be spent in attempting the conventional antegrade approach and escalating through different wires in further antegrade attempts before changing to a retrograde approach to cross the lesion. In a retrograde procedure, access is obtained through vessels distal to the lesion in the foot or ankle in the case of peripheral disease, or through collateral (typically septal) vessels in coronary anatomy. In this respect, retrograde techniques take advantage of occlusions sometimes having a softer distal cap that is easier to cross than a calcified proximal cap. However, retrograde procedures are more complex than antegrade procedures, requiring greater skill and taking much longer to do.

In over 50% of peripheral artery cases, particularly in the popliteal, tibial and peroneal arteries, the vessels are totally occluded by lesions: in approximately 30% of cases the target lesions are severely calcified. These calcified lesions are in effect composed of rigid inelastic segments that typically extend to a length of 3 cm to 5 cm within even longer extensive diffuse lesions that, are, on average, of the order of 20 cm to 25 cm in length. Selecting a treatment for these lesions requires insight as to their length and composition that is not readily available from conventional imaging.

In the case of peripheral arteries, blockages are often too severely diseased and composed of materials too resistant to allow the ready passage of a guidewire. In such instances, the procedure takes substantially longer to complete and may require the use of additional devices to cross the lesion. Quite often, the procedure is eventually abandoned entirely, which prevents preferred follow-on procedures such as balloon angioplasty and stenting and therefore limits the ability to treat the patient.

In view of these drawbacks, there have been several proposals for ultrasonically-activated guidewires and catheters for use in atherectomy or thrombectomy procedures, in which ultrasonic vibrations are transmitted along the element to the distal tip to agitate and to ablate the material of a blockage. The element therefore serves as a waveguide that conveys ultrasonic energy distally. Much of the prior art relevant to the concept of ultrasonic activation in this context is discussed in our previous patent applications published as WO 2020/094747, WO 2021/089847, WO 2021/089859 and WO 2021/224357, whose contents are incorporated herein by reference.

Among other concepts, our previous patent application published as WO 20201094747 discloses a system that comprises an ultrasonic source, an active crossing wire and a signal acquisition, processing and communication chipset or control circuit. The chipset or circuit can generate signals for controlling the system and can provide outputs to users and/or external data acquisition systems. In particular, a controller monitors measurements of frequency and amplitude of current and voltage at the source and of incident, reflected and standing waveforms in the wire and thereby estimates displacement of the distal tip. Modulation of those variables is monitored as the wire transits through the anatomy and crosses through different types of occlusions, including calcified CTOs. This enables determination of calcific versus non-calcific lesions and of the duration or length of a calcified segment of a lesion. A user can then react to control the system or the system can control itself accordingly, for example by increasing input, power on encountering a lesion that is determined to be calcific.

WO 2020/094747 proposes that a digital signal processor interrogates the measurements made, provides feedback and interprets and compares the relative contributions of losses from anatomical tortuosity in navigating to the site versus those arising from passage through the occlusion. The system processes data obtained from measurements that are indicative of the ultrasonic waveform as transformations of the resonant vibrations occur while passing through the vasculature and through occlusions. Algorithms transform the raw data into procedurally relevant outputs. The system can compare and interpret the difference between calculated values from the active system and a prescribed set of values to characterise the nature of a material occluding the vessel.

Thus, the system of WO 2020/094747 considers variations in characteristic losses that are typical of engagement of the active wire with different healthy and diseased tissue types. There is differentiation between losses in the vessel and losses associated with lesions and between lesions of different composition, especially between calcified and non-calcified lesions. The characteristic response to differential changes occurring in different media and in the passage or navigation of the endovascular wire through different anatomies is used to create distinct algorithms that are used to: 1) determine the source of, and to compensate for, losses in the system; 2) assess the tone of arterial vessels; and 3) determine the composition detail of a lesion. These algorithms may, for example, provide compensation to the tip of the wire as it comes into contact with compliant, non-compliant and calcific material and in the latter case may amplify the energy input to the system accordingly.

The present invention takes WO 2020/094747 as its starting point. The invention seeks to improve the quality of feedback concerning the behaviour of an ultrasonically-energised elongate waveguide element, such as a wire, as the element traverses and interacts with the anatomy and with any obstructions or other lesions encountered in the anatomy. In this respect, it has been found that when in situ and activated, the element will produce characteristic acoustic signatures indicative of different properties that characterise a lesion, the tissue of a vessel and possibly also the flow of blood along a vessel.

Thus, the invention resides in endovascular apparatus for determining the condition of a vessel in a body, including any lesion in that vessel. The apparatus comprises: an elongate waveguide element; an activation unit comprising a source of ultrasonic energy and a coupling for coupling the source to the waveguide element to activate the waveguide element, thereby transmitting ultrasonic energy from the source along the waveguide element to an active distal section of the waveguide element; and a signal acquisition system that is configured to acquire feedback signals from the apparatus for use in interpreting vessel condition. The signal acquisition system comprises at least one acoustic sensor for acquiring acoustic feedback signals generated by the apparatus when the waveguide element is activated. At least two acoustic sensors may be spaced longitudinally from each other.

At least one acoustic sensor may be mounted in or on the activation unit, for example in longitudinal alignment with, or proximally relative to, or distally relative to, the coupling of the activation unit. At least one acoustic sensor may be mounted on or parallel with the waveguide element, for example proximally or distally relative to the length of the waveguide element.

The waveguide element may be, or may comprise, or may be surrounded by a catheter, in which case at least one acoustic sensor may be mounted, on the catheter. Additionally, or alternatively, the waveguide element may be or may comprise a wire, in which case at least one acoustic sensor may be mounted on the wire. A strain gauge may be fixed to the waveguide element, such as a wire, to acquire operational feedback signals from the waveguide element, Such a strain gauge could serve as an acoustic sensor.

A least one acoustic sensor may be an extra-corporeal sensor arranged to lie against a part of the body or may be an intra-corporeal sensor arranged to be inserted into the body.

In preferred embodiments, the signal acquisition, system further comprises at least one electronic sensor that is configured to acquire operational feedback signals representing operational parameters of the source of ultrasonic energy. Those operational parameters could be frequency and/or amplitude and/or phase of current drawn by, or voltage dropped across, the source of ultrasonic energy. The signal acquisition system may be configured to monitor variations in frequency or amplitude of vibration of the waveguide element via the coupling.

The apparatus may further comprise a signal processing system for processing feedback signals acquired by the signal acquisition system. Such a signal processing system could, for example, be configured to employ numerical algorithms selected for specific types of the waveguide element.

The signal processing system may be configured to determine characteristics of an obstruction in a vessel from the acquired feedback signals. The signal processing system may also be configured to compare relative contributions of losses from anatomical tortuosity in navigating the active distal section to an obstruction versus losses arising from the passage of the active distal section through the obstruction.

The signal processing system may be configured to compare the acquired feedback signals with stored data that characterises known obstructions, and to characterise an obstruction with reference to that comparison.

The signal processing system may further comprise an output to a user interface and/or to an external data acquisition system, and/or an input from a user interface and/or from an external data network.

The apparatus may further comprise a controller that is responsive to the signal processing system. Such a controller could be configured to modulate excitation voltage applied to, or excitation current supplied to, the source of ultrasonic energy. The controller may, in particular, be configured to control the source of ultrasonic energy by varying frequency and/or amplitude of the excitation voltage applied to the source, of ultrasonic energy. The controller could also be configured to drive the frequency of the excitation voltage by employing a phase difference between the excitation voltage and the excitation current in conjunction with amplitude of the excitation voltage.

The controller may comprise an amplitude feedback controller and may be configured to use a resonant frequency as an operating point of control. The controller may be configured to pulse or vary a drive signal to the source of ultrasonic energy.

The controller may be configured: to monitor modulation of transmitted signals and to control the source of ultrasonic energy automatically to compensate for background energy loss encountered in the waveguide element as the active distal section approaches an obstruction; and to distinguish the background energy loss from additional energy loss, as the active distal section passes through the obstruction and to compensate for the background energy loss to sustain displacement at the active distal section.

The controller could be configured to modify or change a control algorithm in response to variation in operational parameters of the source of ultrasonic energy arising from interaction of the active distal section with an obstruction in use.

The inventive concept embraces a communication system comprising the apparatus of the invention in data communication with a computer system that is arranged to receive data from the apparatus, to optimise and update control algorithms accordingly and to output the optimised, updated control algorithms to the apparatus. Optimally, two or more such apparatuses are in data communication with the computer system, which is therefore arranged to optimise control algorithms in accordance with data received from multiple procedures performed using the apparatuses and to output the optimised, updated control algorithms to the apparatuses.

The inventive concept also embraces a corresponding method for determining the condition of a vessel in a body. The method comprises: navigating a distal section of an elongate waveguide element to a site in the vessel; activating the waveguide element by transmitting ultrasonic, energy to the distal section; acquiring acoustic feedback signals generated when the waveguide element is activated; and interpreting the acoustic feedback signals to characterise the condition of the vessel.

The method of the invention can assess decay in amplitude of, or a shift of frequency of, displacement of the waveguide element caused by losses resulting from contact with a wall of the vessel or with material in the vessel such as an occluding lesion.

The distal section of the activated waveguide element can be engaged with a lesion in the vessel, and consequential changes in the acoustic feedback signals can then be interpreted to characterise the lesion. Conveniently, the distal section the activated waveguide element can also disrupt the lesion.

The method may further comprise comparing sensed data representing the response of the activated waveguide element to the lesion with stored data representing the response of a corresponding activated waveguide element to interaction with a known lesion.

Acoustic feedback signals may be acquired in an extra-corporeal activation unit disposed proximally of the waveguide element, and/or at one or more locations along the waveguide element, and/or at an intra-corporeal distal location along the waveguide element, and/or at one or more locations outside the vessel, and/or at two or more locations longitudinally spaced from each other.

Preferably, the method further comprises acquiring non-acoustic feedback signals representing operational parameters of a source of ultrasonic energy coupled with the waveguide element, or more generally obtained by monitoring variations in frequency or amplitude of vibration of the waveguide element. It can be determined from the operational parameters how the source responds to the waveguide element encountering the vessel and any lesion in the vessel. For example, the non-acoustic feedback signals may represent variations of frequency and/or amplitude and/or phase of current drawn by, or voltage dropped across, the source of ultrasonic energy. Conveniently, damping of the waveguide element can be determined by monitoring decay of a current signal over time.

Data sets can be generated from the acoustic and non-acoustic feedback signals, allowing combinations of, or comparisons between, the respective data sets to be used characterise the condition of the vessel. Amplitude or frequency of the ultrasonic energy transmitted to the distal section along the waveguide element may be adjusted in response to the non-acoustic feedback signals. Also in response to the non-acoustic feedback signals, the source may be controlled to maintain a resonant frequency in the waveguide element.

The method of the invention may comprise: outputting data to an external data network; receiving data from the network in response; and, on receiving data from the network, modifying or changing a control algorithm accordingly. The method may also comprise: outputting data to an external computer system; in the external computer system, optimising and updating a control algorithm in accordance with that data; outputting the optimised, updated control algorithm from the external computer system; and using the optimised, updated control algorithm to control activation of the waveguide element. Preferably, the computer system can optimise the control algorithm in accordance with data received from multiple procedures.

Two or more different waveforms can be applied sequentially to a source of the ultrasonic energy, those waveforms being selected from, for example, sinusoidal, pulsed, multitone, chirp or noise waveforms.

To improve sensitivity, the method can comprise: advancing the distal section of the activated waveguide element close to a lesion in the vessel; acquiring baseline feedback signals; advancing the distal section of the activated waveguide element into engagement with the lesion; acquiring operational feedback signals; and subtracting the baseline feedback signals from the operational feedback signals.

In summary, the invention involves acoustic characterisation of the effects of intraluminal elements such as ultrasonically activated wires. In particular, the invention employs an ultrasonic waveguide device such as a crossing wire not only to excavate a lesion and to disrupt calcified intralumenal or intramural plaques within the vessel but to determine the characteristics of a vascular lumen. Those characteristics may include the internal diameter of the vessel, the vascular tone of the vessel and the mechanical characteristics and composition of any material blocking the vessel.

In WO 2020/094747, the inventors proposed that different wires having known characteristics, such as specific combinations of ground tapered profile, land length and diameter, will respond to a lesion in a way that can discriminate between lesions of a calcific or non-calcific nature. The inventors have now determined that further analysis and processing of spectra can provide for more sensitive assessment of a lesion and/or of other surfaces that the wire may contact within the vasculature. More specifically, the invention aims to allow assessment of the internal diameter of a vessel and to characterise, through interpolation, the mechanical properties of the vessel wall and any materials that may be blocking the vessel. Thus, the invention enables identification of whether a blockage is composed of a gelatinous plaque, calcific material, a thrombus or some other form of embolic material. Of particular interest is to determine whether the blockage is of a vulnerable soft plaque or a calcified plaque or, if the blockage is a thrombus, to characterise what type of thrombus is present.

In examples to be described, a system of the invention comprises a wire that is manufactured with a specific ground profile toward its distal end and whose longitudinally successive sections have specific diameters and lengths. Examples of such wire characteristics are taught in our aforementioned prior patent applications. They enable a distal end portion of the wire to activate in a particular way, at the resonant frequency (and harmonic frequencies associated with or consistent with the resonant frequency) of the piezo-electric ultrasonic transducer that activates the wire.

A coupling mechanism enables the wire to be coupled to the transducer. The transducer is driven by an ultrasonic signal generator that can excite the transducer and hence the wire at a desired frequency and amplitude. A control circuit monitors and controls the electrical load across the transducer to effect the desired actuation.

In accordance with the invention, at least one acoustic sensor detects, and so in effect listens to, acoustic emissions from the wire, the coupler and/or the transducer. The system can monitor and analyse the detected acoustic, spectra and can present processed information to the user in a meaningful way. Acoustic information may be used in conjunction with other information, such as inputs to or outputs from the control circuit, to improve the quality of analysis detection and determination. Processed information may also be stored in and shared from an external database, such as in the cloud, the better to educate physicians and to perfect analytical algorithms with a growing sample size representing use of the invention in actual procedures.

The invention exploits the insight that interpretation of acoustic spectra emitted during the passage of a vibrating wire or other waveguide through vascular anatomies can provide a means to interpret characteristics of tissues. This is possible because when the wire comes, forcefully, into contact with any surface, such as the inner surface of a vessel or a lesion blocking the vessel, that contact will modulate the frequency and/or the amplitude of the acoustic waveform travelling though the wire. It is possible to associate those modulations with particular characteristics of the vascular anatomy. It is also the case that at such ultrasonic high frequency, interactions with the vessel wall will disrupt calcified materials within the wall, thus at once assessing vascular hardness as well as softening plaque.

It is also possible through interrogation of the acoustic spectra alone, and/or through other inputs from the environment, to interpret from transformations in the wire what structures or materials the wire may be contacting as it passes though the internal morphology of a vascular lumen. This includes any blockage that may be in the lumen, or, if the wire is excavating or removing any such blockages, the character of the blockage.

A basis for making such an assessment is that the amplitude of any axial or radial displacement associated with resonance in the system varies with input amplitudes and its decay, or displacement of frequency, is associated with losses resulting from the wire coming into contact with other materials or surfaces at its end or along its length. These changes in the acoustics detected along, the wire can be used to characterise the vessel, its lumen and any obstruction. Further, as impedance in the transducer may also modulate as a result of changes in the losses in the system as the wire is damped or becomes more or less constrained, superimposition of this electrical response can be used to analyse and describe the characteristics of the vessel, its lumen and any obstruction more accurately:

One or more acoustic, sensors may, for example, be positioned on, in, or close to a housing of the transducer, or on a wire, or on a catheter, or in, or in contact with, the patient's body in order to detect sounds being emitted and to subtract surrounding noise. The resulting acoustic spectra are processed and analysed by an algorithm that recognises sound spectra characteristic of specific types of interference and resonant and sub-harmonic frequencies. As noted above, the sensitivity of the acoustic algorithm may be increased by interrogating variations in electrical signals used to drive the transducer at its resonant frequency.

The acoustic spectra are compared by the system to the ultrasound spectra in a device that employs an intravascular waveguide, such as a wire, resonating at a frequency and amplitude that allows the distal end portion of the wire to resonate with axial and radial displacement. In the context of a crossing wire, the primary purpose of those displacements is to excavate through materials occluding a vessel. The invention uses those displacements for another or additional purpose, namely to generate an acoustic signal that varies in different ways on travelling, through the vasculature and on encountering and engaging with a lesion. The acoustic signal also varies in different ways on engaging with different types of lesion, hence serving as an acoustic signature that characterises the lesion.

As explained in our aforementioned previous patent applications, the dimensions and profile of a crossing wire allow the wire to resonate at harmonic and sub-harmonic frequencies with various modes of displacement, particularly in its distal end portion, Modulation occurs as the wire comes into contact with different surfaces. For example, when the distal tip of the wire encounters a calcified blockage that restrains its lateral displacement, the mode of displacement of the wire will transition from 'fixed to free' to 'fixed to fixed'. 'Fixed to free' may be visualised as a node at the proximal end of the wire and an antinode at the distal end of the wire whereas 'fixed to fixed' may be visualised as a node at both the proximal and distal ends. This modulation will shift the wavelength slightly and therefore change the acoustic signal transmitted by the wire.

Analysing changes in wavelength allows the system to sense what type of materials have disturbed its wavelength and frequency and therefore to determine the type of materials with which the distal end portion of the wire is in contact. Thus, interpretation of the acoustic spectra emitted during the passage of waveguides through vascular anatomies can provide a means to interpret characteristics of the tissue with which the wire comes into contact. It can also interpolate, through mathematical transformations, features of acoustic spectra or electrical signals indicating how the wire is responding to the internal morphology of the lumen in removing any blockages in the vessel.

As the system is dynamic, characterisation of the manner in which the system responds needs to be done dynamically to be true to comparisons between electronic control and acoustically-emitted variables. The dynamic interrogation and subtraction of features, or addition in the case of patterned excitation, needs be monitored in time. In this respect, feedback may be interrogated from compared programmed inputs such as pulses or patterns to seek variations of specific features. Feedback may also be interrogated from compared variations over time, such as a quality factor or Q factor representing damping.

Thus, the invention embodies principles of acoustic characterisation, proposing that an active element such as a wire in situ within a vessel will produce characteristic acoustics as it comes into contact with the vessel wall and with any blockage, whether a thrombus, soft or fibrous, or an atherosclerotic lesion, hard or soft, in the lumen or in the wall of the vessel. The captured acoustic signature will be characteristic of the lumen of the vessel and the surrounding tissues. It is proposed that through direct comparative measurements interpolated or extrapolated, it will be possible with post-processing analysis and suitable algorithms to produce a reliable diagnostic output to associate these characteristic acoustic spectra with the nature and integrity of the tissues.

Preferred embodiments of the invention employ two sensors in operation simultaneously, namely an electrical or electronic sensor and an acoustic sensor.

The electronic sensor acts on features such as the transducer that generates ultrasonic energy and determines how the transducer is operating, setting the scope of its ability to sense and produce data that may be interrogated. The electronic sensor also detects the electrical drive frequency and the ways in which the system responds to variability or instability introduced by the wire moving through tortuous vessels up to the point of the lesion. The electrical drive frequency is modulated by encounters with vessel walls and blockages in the lumen. Driver electronics respond to this by tracking variables of phase angle, current and/or voltage. The invention contemplates interrogation of this dynamic control variation in the main variables, to provide characteristic features that can be associated with the physical characteristics a vessel and any blockage within it.

One or more acoustic sensors, or microphones, listen for all, or a portion of, the acoustic emissions through and from biological tissues when the active wire is in viva, whether intramurally, intraluminally or extra-corporeally. The acoustic sensor, in particular, listens for acoustic emissions from the wire actuated internally within the lumen of a vessel. The invention enables interrogation of variations in acoustic emissions affected by interference between the wire and the vessel or anything in the vessel, such as a OTO.

The data set from acoustic sensors is much richer than the data set from the small range of operational frequencies used in activating the wire, even though the acoustic emissions are created by that small actuating range. The result is a huge amount of additional data that can be mined using various mathematical instruments to find features and then to associate those features with the nature of the vessel and its contents, the behaviour of the wire and the nature of a new channel excavated by use of the wire. Thus, the electronic data set can be enormously enhanced by the integration of acoustic data.

Interrogating the full range and the spectrum all of the different frequencies that are being expressed requires significant post-processing assessment, hence a preference for a cloud-based, machine-learning approach to operation, development and updating of advanced algorithms. However, a suitably programmed on-board processor facility, in the local device, would be able to manipulate the data through suitable algorithms to provide at least 'binary' feedback, such as whether a lesion is calcified or non-calcified or hard or soft. It is emphasised that post-processing of any form, whether in the cloud or otherwise, is not a requirement. Such processing may be performed locally, in real time.

Disclosed, therefore, is an ultrasonic system that induces vibrations in customised endovascular surgical wire devices and interrogates and applies artificial intelligence to acoustic feedback and optionally also other feedback in the system. The feedback can be used to optimise the performance of the system in navigating to, crossing through and characterising and modifying the structure and properties of endovascular occlusions.

A programmable circuit system for data acquisition and processing and for controlling activation of the system may include an integrated, or on-board, programmable digital signal processing chipset. This processes the monitored, transmitted and received or incoming acoustic and/or electrical or electronic signals using algorithms to: interrogate the response; compare the ultrasonic feedback and the effect on the resonant frequency standing wave; estimate the size of the opening tunneled though the lesion by the activated tip; and modulate the power in the system via voltage amplitude and system frequency.

Analog and digital signal analysis and power control of the device as well as communications modules enable wired and wireless connection of the device and its data to wider data networks and the internet. This may, for example, facilitate development of more intelligent algorithms to manage the system.

As ultrasonic vibrations are transmitted via the transmission member serving as a waveguide, the distal tip of the transmission member vibrates at a prescribed frequency and amplitude with the capability of beneficially disrupting the diseased tissue or other material. The digital signal processing and control circuitry responds to acoustic and other feedback to allow semi-autonomous gross characterisation of the lesion, power control and the estimated size of opening in the system.

When the ultrasonic system is activated, the emitted waves travel along the wire to its distal tip where they are reflected or transmitted through to neighbouring materials. Reverberations created in the wire at different transitionary points establish a series of secondary and tertiary reflections. These waves are characteristic of different wire designs and features and they can be optimised to heighten the difference in the features of their signals. The reflections are determined to be composed of a specific pattern of response in the waveform at any time for a given input and their variation is associated with perturbations or differences in the ambient environment. The waveforms give rise to characteristic acoustic emissions that can be used in isolation or in addition to other feedback signals.

The amplitude of displacement along the wire, at specific frequencies, varies through the course of a procedure as a result of damping from contact with surrounding tissues, either during navigation to the site of a lesion or in contact with diseased, non-compliant or calcified tissues in a lesion. The reverberations in the system and resulting acoustic emissions are similarly affected, in characteristic ways, that allows their use in characterising the source and the nature of whatever is causing damping.

To effect a constant vibration amplitude, the ultrasonic transducer is controlled by a suitable feedback controller. In the case of the ultrasonic waveform, phase feedback control and comparison can be made by an electrical equivalent model such as the Butterworth-vanDyke model.

The ultrasonic transducer can be controlled by the frequency and the amplitude of the excitation voltage. Changing the frequency may influence the phase between the voltage and the current. The amplitude of the excitation voltage that controls the current is proportional to the vibration amplitude in resonance. This allows control algorithms to employ only phase and amplitude to drive frequency.

In a preferred embodiment, the approach is to drive the system using the resonance frequency as the operating point of control, in conjunction with an amplitude feedback controller, managing this operation through the use of customised programmed control algorithms that are unique for each wire type.

The advantages of a resonant driven, low damped system are the low voltages necessary and the high values of effective power. This, solution also offers advantages in controlling the response of a Nitinol wire to ultrasonic activation.

Temperature effects in Nitinol and changing load conditions during a procedure due to interaction with surrounding tissues that can potentially result in a change of resonant frequency and vibration amplitude can be, compensated for, within a range, for a given transducer.

Thus, in terms of the use of voltage and current, control and analysis through the resonant frequency may be used to monitor differential changes, over time and length, and this interrogation and compensation may be used to characterise the nature of the endovascular anatomy. The ability to capture the acoustic emissions from the interaction of the system with the neighbouring tissues provides for an additional and separate means of inferring, the nature of, or characterising, the tissues, as their response to the interaction with the wire will be determined by their structural properties.

The comparison and analysis of and between the primary emitted signal and the tertiary feedback responses in the wire considers variations in characteristic losses, typical with the engagement of the active member with different, healthy and diseased, tissue types. It differentiates between these types of losses in the vessel and those associated with lesions between lesions of different composition, for example between calcified and non-calcified lesions.

The resistance load encountered and the acoustic emissions recorded by the system vary. As the active member passes though different anatomies, analog signals may be interrogated by an on-board digital signal processor, conditioned and the parametric output processed by algorithms to add to data from acoustic feedback to characterise response, to define feedback and to effect control.

Algorithms may be customised to attune to the wire type. The range and the rate of change and the differential order of the change, filtered by the signal processing circuit, may be used by an algorithm to characterise the nature of the material through which the wire passes. This may then be communicated to the physician as the procedure is being undertaken to assist in defining therapy.

To improve performance, algorithms may be trained by bench ex-vivo and in-vivo data. The latter possibility is enabled by a communications model that provides for the transportation of data to and from the device. The system can enable, wired or wireless communication of data between the device and another device or cloud service for analysis and storage.

Thus, the quality of the operation and interpretation by the device can be improved over time by the interpolation of more data sets from additional procedures that builds upon the use experience. Such data can inform the design of iterative generations of control and interpretation algorithms. Consequently, onboard, local and/or cloud-based refinement of algorithms can improve the design and operational interface of a treatment device and can provide more detailed, feedback to a physician using the device, in addition to customising the operation of the device to suit different wire geometries and anatomies.

The frequency at which the transducer generates a mechanical signal may be at a set short-range frequency sweep, over a short range of frequencies, to accommodate losses from interaction and impingement by different forces over the length of the wire. The speed of the microprocessor allows the device to process, small fluctuations in resonance in real time.

The signal used to drive the ultrasonic generator may be pulsed or varied to reduce heating and to optimize analysis and matching of offsets at the resonant frequency. For example, a pulsed modulation of voltage, over a small frequency range, can activate the crossing wire and a digital signal processor unit can interrogate the measurements made, provide feedback and interpret and compare the relative contributions of losses from anatomical tortuosity in navigating to the site versus those arising from passage through the occlusion.

The invention employs methods to, interrogate feedback signals to characterise the vessel or lesion through which the wire is crossing and to collect data on the lesion being crossed, such as its length and composition which are facets that inform the manner in which the target lesion may be treated by the physician. This data may also be provided as feedback to the physician in a haptic and/or visual and/or audio form on a display to help the physician to operate the device. For example, this feedback could allow the physician to monitor a crossing procedure, using a simple, backlit screen on the compact activation unit to display and assess the character of the lesion.

In another embodiment, where a user has access to a network, data from the procedure may be captured anonymously to protect patient confidentiality and communicated from the device to a data storage and processing platform where it may be analysed in real time or later Characterisation of the lesion may also be presented to the user for their analysis and interpretation while conducting the procedure.

An attachment may be used to record and measure displacement of the wire as it traverses the vasculature and to map that data against lesion composition from feedback to characterise the properties of the lesion as a function of displacement through the lesion.

The variation in the magnitude of the input and control parameters of current, voltage and frequency with the characteristic capacitance of the converter provide a matrix of measurements and controls that can be used in conjunction with acoustic feedback to determine the power and characterise the lesion being crossed.

Monitoring acoustic emissions and electronic response such as current may support interpretation of the lesion and modulation of voltage allows for the amplification of power and the recovery of frequency as the device actuates the contact surface and reduces offset. This array of measurements in the small frequency range then allows for gross characterisation of the composition of the lesion, be it calcified, fibrous or gelatinous over all or part of its length. These interpolated characteristic components are not absolute characteristics of the lesion but are instead indicative of: composition; degree of calcification; and whether the lesion is rigid, compacted or disaggregated. This can be indicative of the nature of the lesion and inform the physician of the optimal therapy to consider. This may, for example, help to determine whether the composition or consistency of the lesion is compacted calcific particulate, or non-compacted fibrotic, or hard or soft gelatinous.

A specific algorithm, for each standard wire type, could be employed to estimate the diameter mapped out by deflection of the distal tip when excited at different levels of frequency and power and device configuration in the conditions pertaining to the procedure. This provides an estimate of the diameter of a resulting tunneled channel through the occlusion.

The system may process data obtained from measurements of the ultrasonic waveform as it is generated, as the waveform passes through the wire or other transmission member, as transformations of the resonant vibrations occur, and as the reflected waveform is attenuated by a transmission member, while passing through the vasculature and through occlusions.

Monitoring and analysing modulation of transmitted signals can automatically adjust for energy losses in the system through voltage control to increase power in the system and compensate for energy losses encountered in the wire as it is passes through the vasculature to the occlusion. Monitoring and analysing modulation of transmitted signals can also distinguish these losses from additional losses as the wire passes through the occlusion and to compensate those additional losses to sustain the displacement at the distal tip.

The measured parameters and variables may be operated on numerically to determine their rate of change relative to each other and other parameters. Differences between these calculated values from the active system and a prescribed set of values can be compared and interpreted numerically to characterise the nature of a material occluding a vessel.

In order that the invention may be more readily understood, reference will now be made, by way of example, to the accompanying drawings in which:

FIG. 3b represents fundamental complex waveforms generated from the harmonic waveforms of FIG. 3a:

Figure 1:
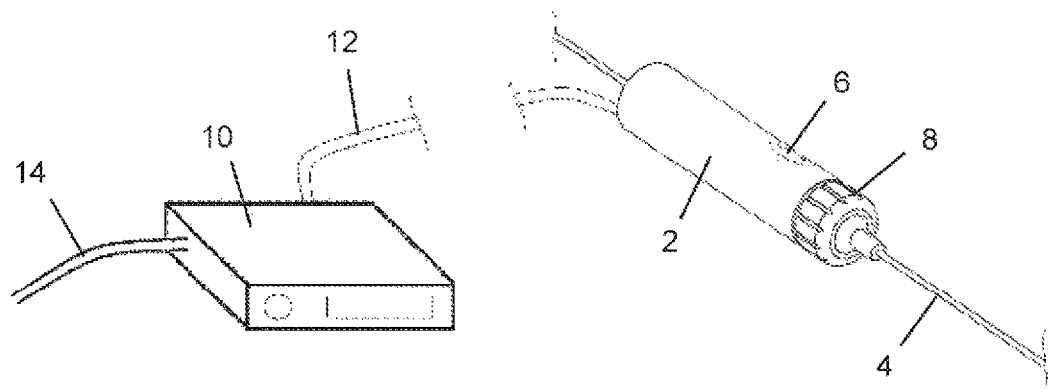
FIG. 1 is a perspective view of apparatus that implements the invention.
Figure 6:
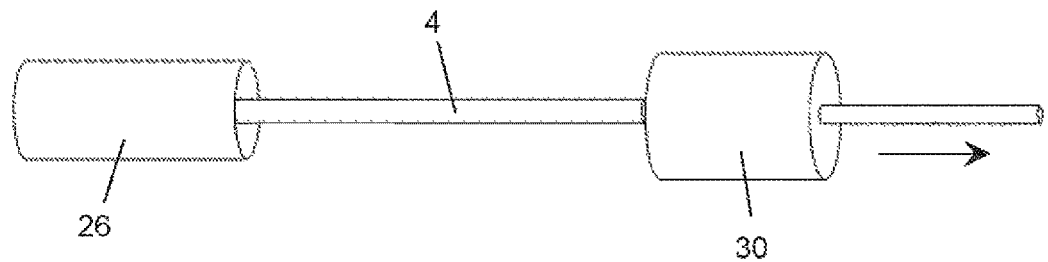
Figure 7:
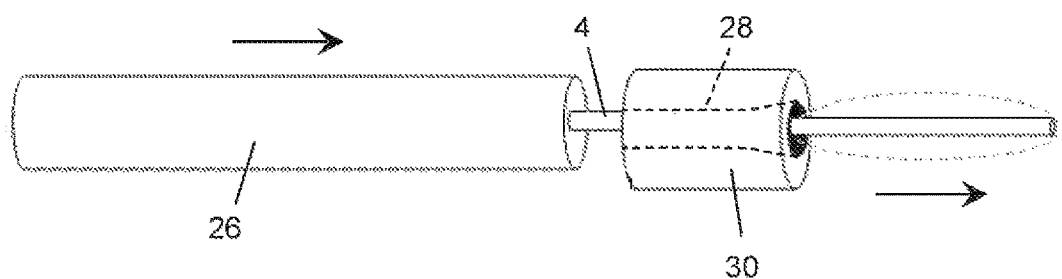
Figure 9:
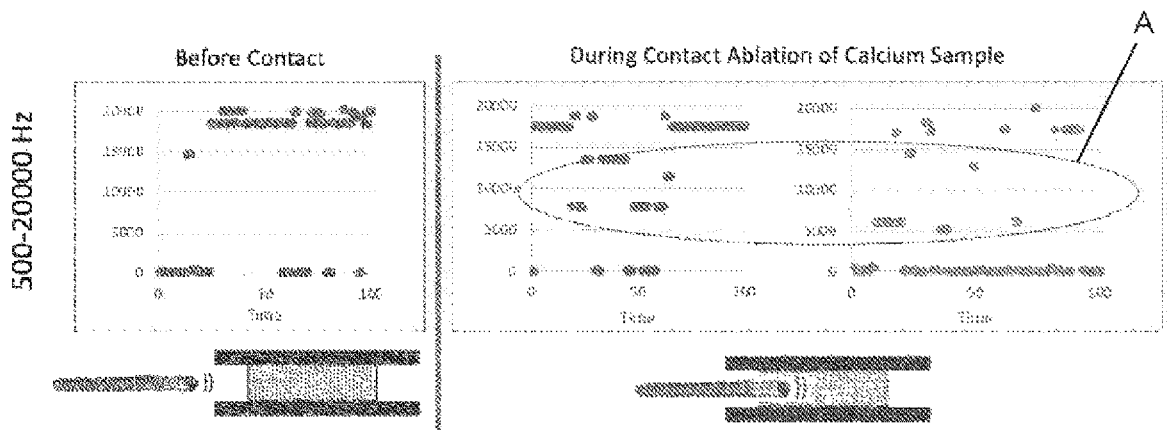
Figure 10:
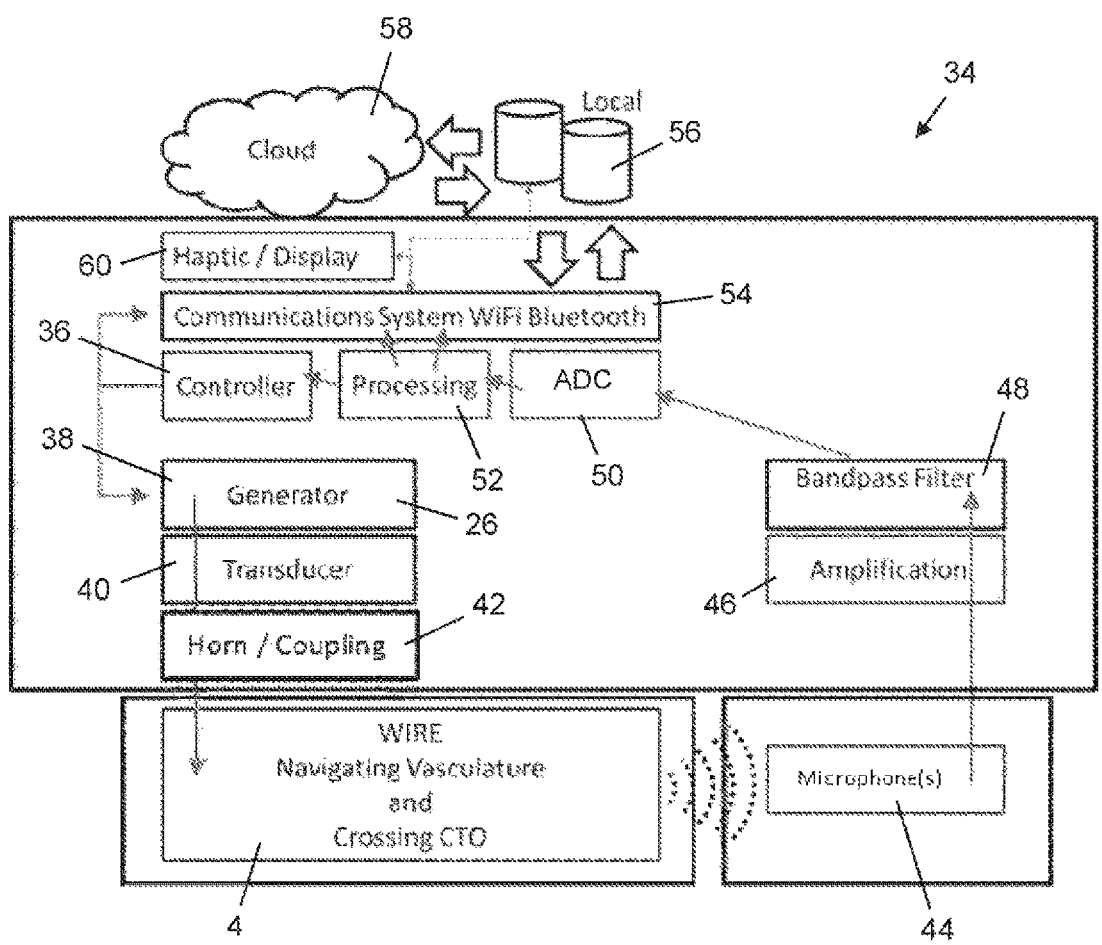
Figure 11:
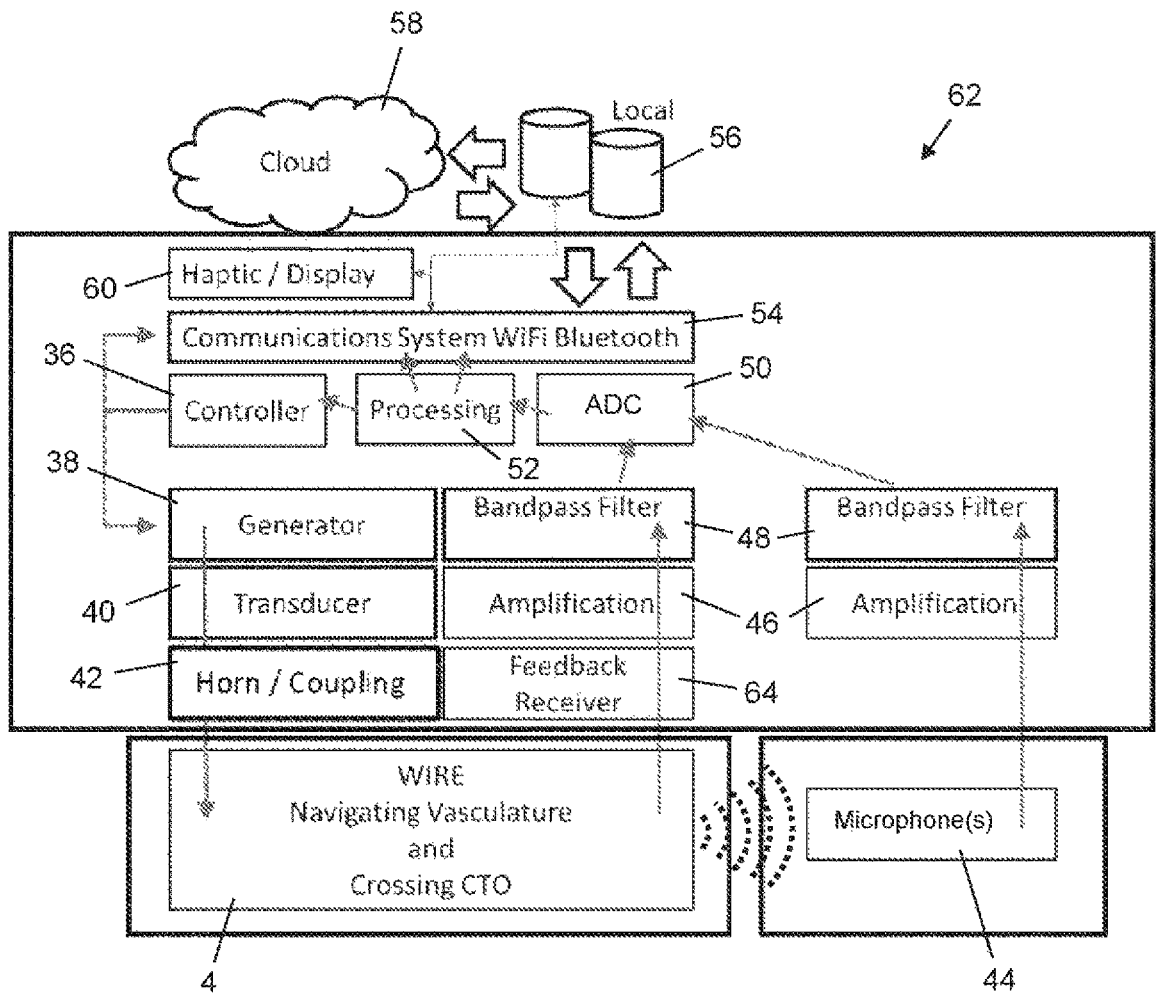
Figure 12:
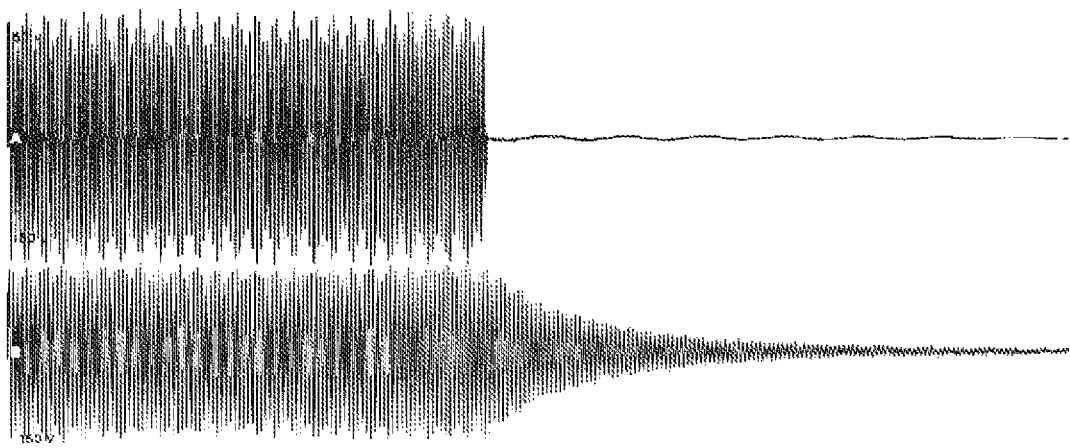
Figure 15:
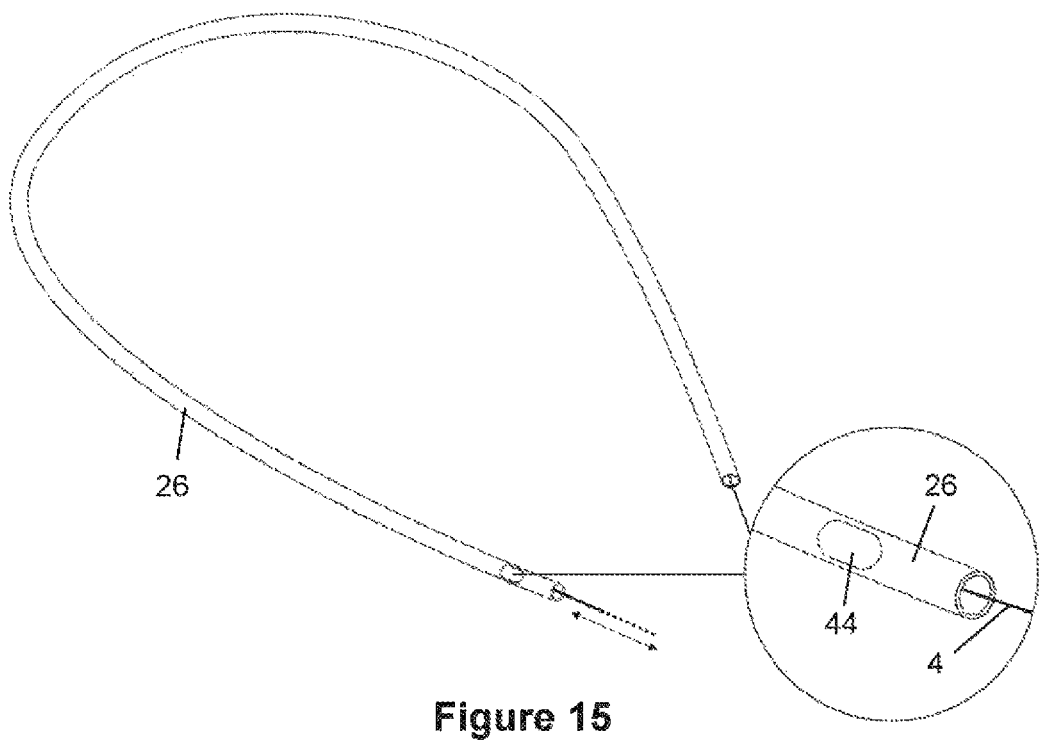
Figure 16:
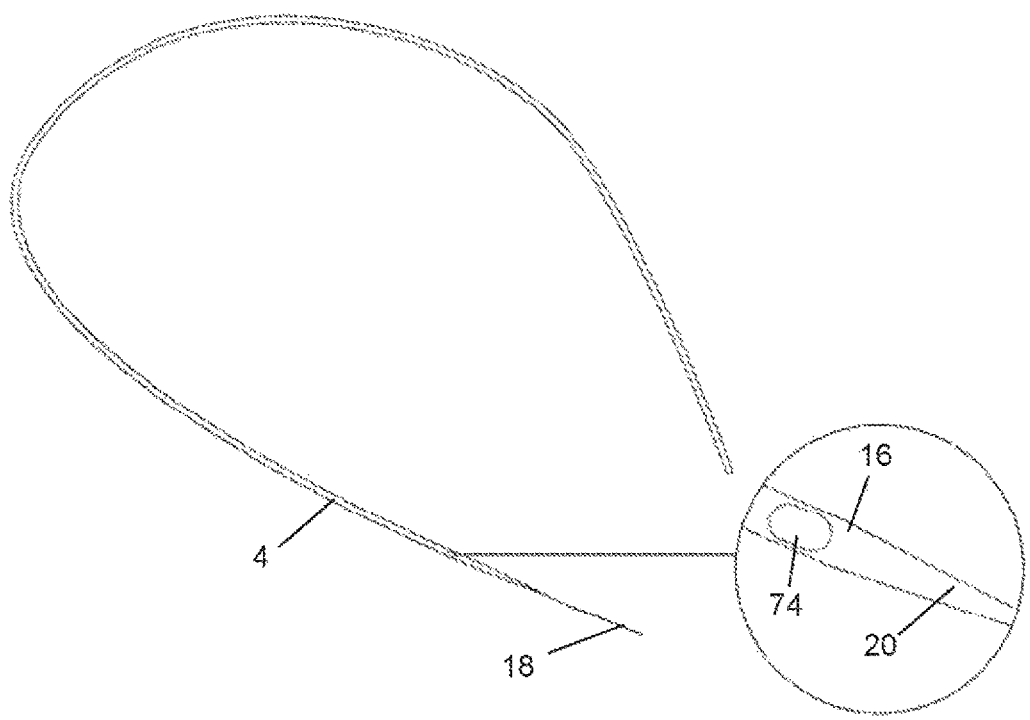
Figure 17:
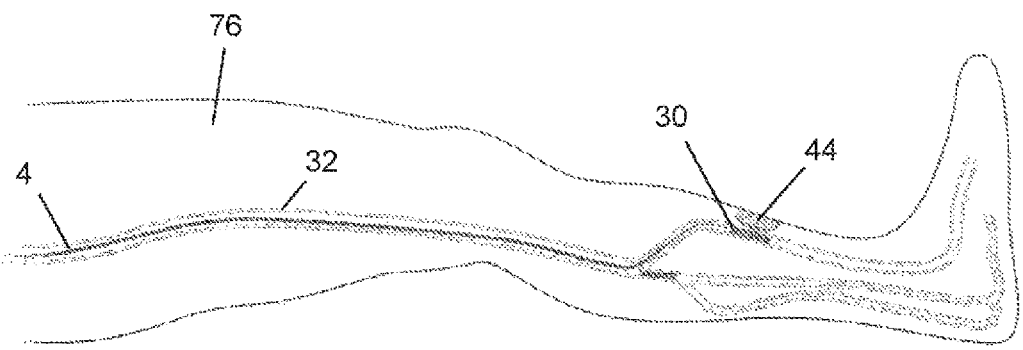
Figure 18:
Figure 19:
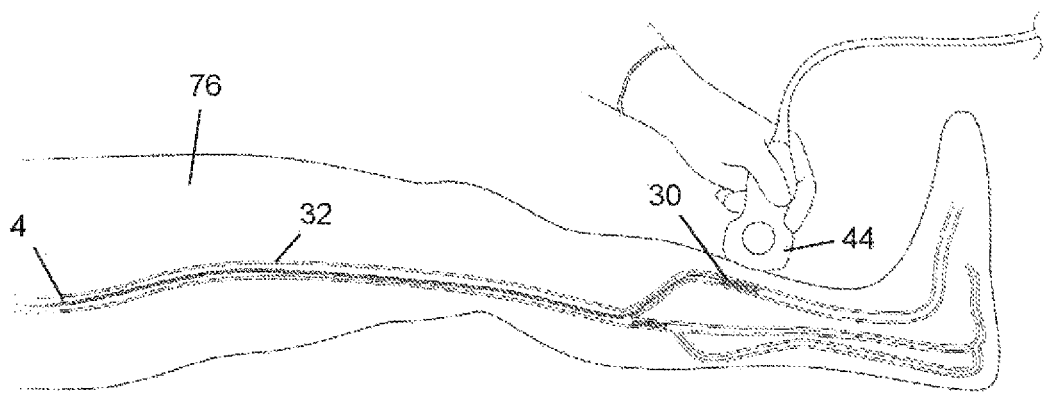
Figure 20:
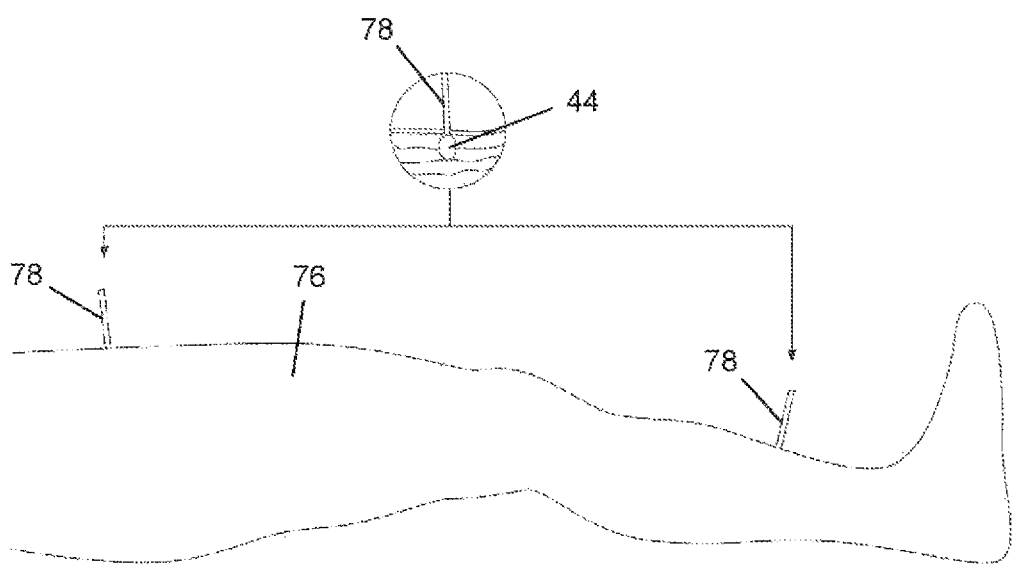
Figure 21:
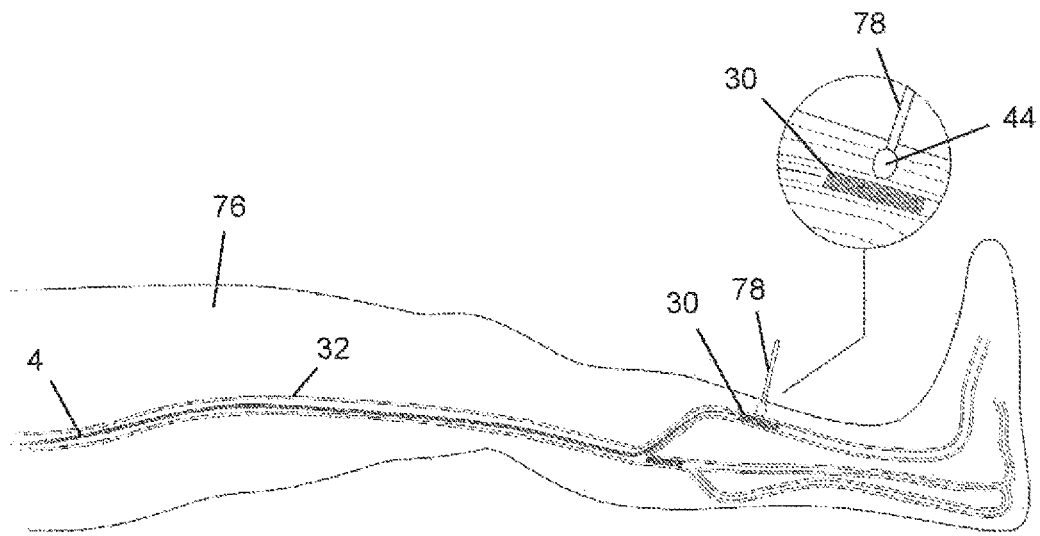
Figure 22:
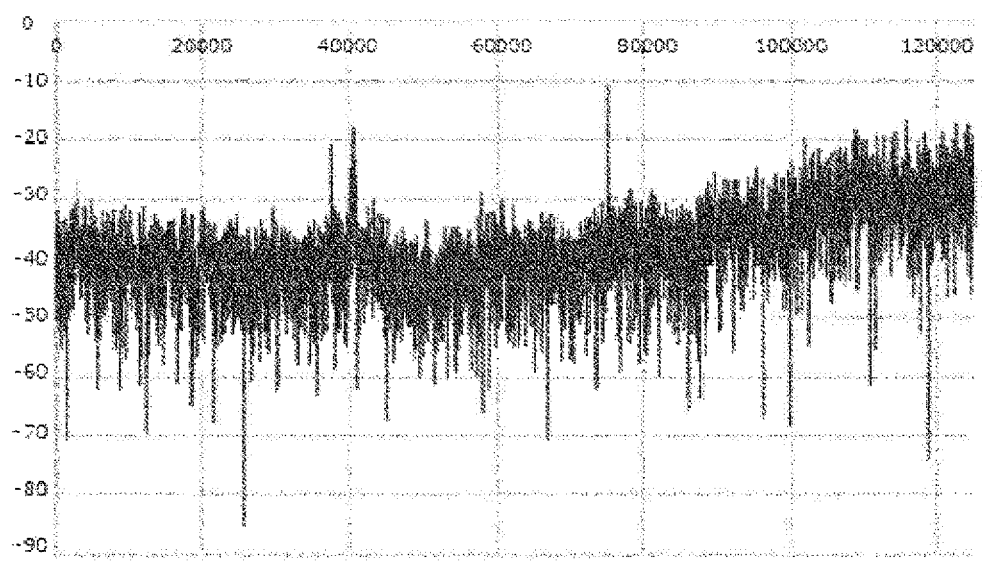
Figure 23:
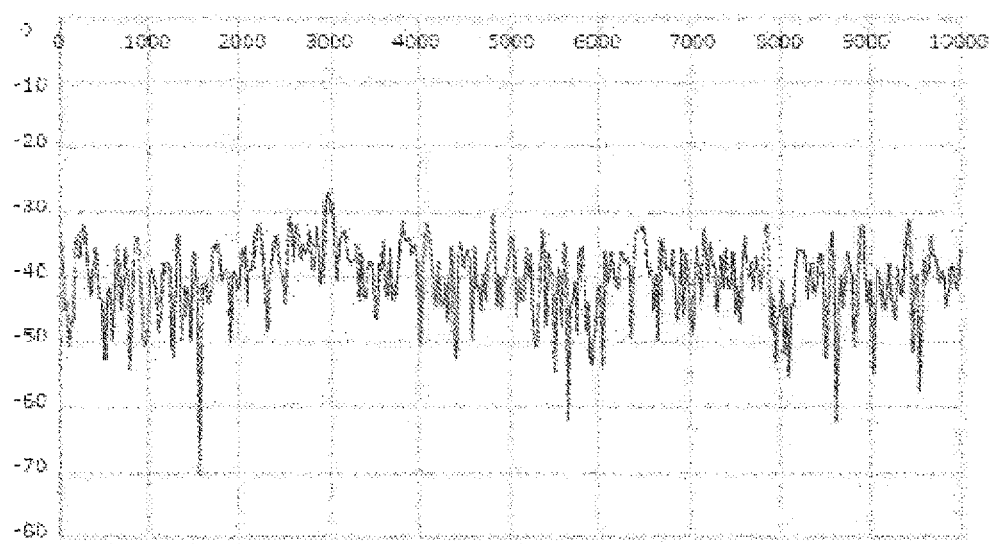
Figure 24:
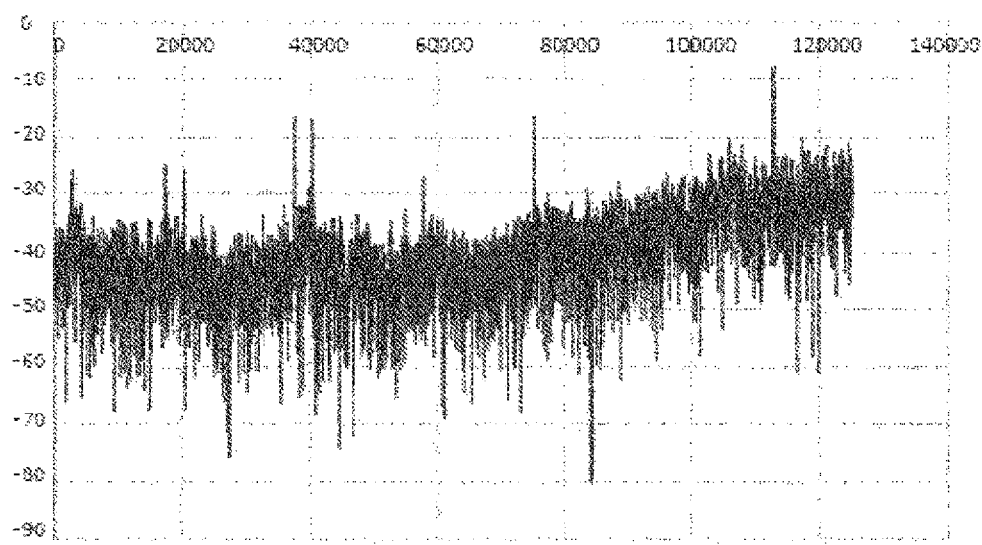
Figure 25:
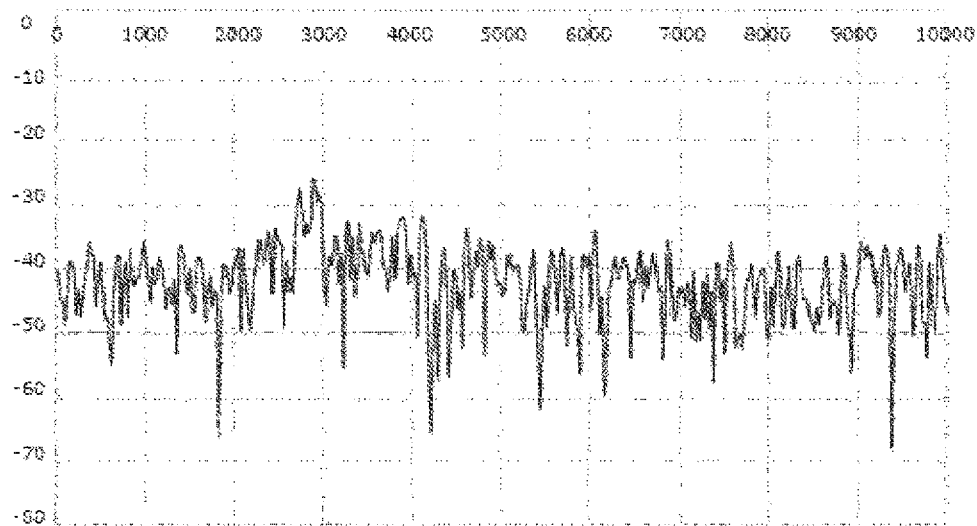
Figure 26:
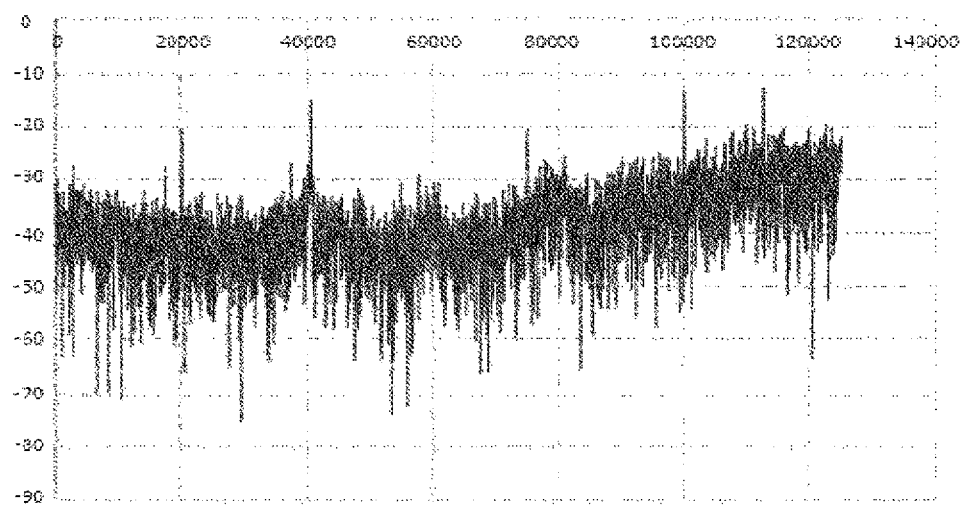
Figure 27:
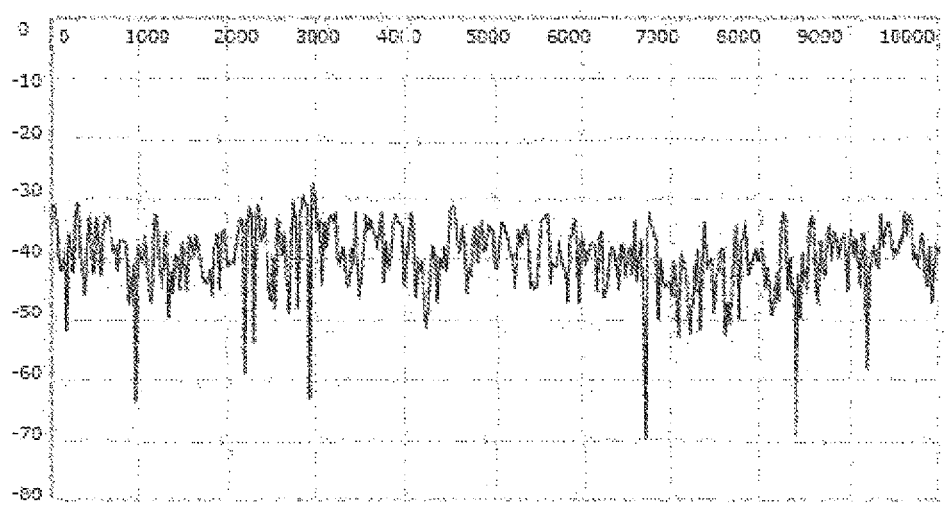

FIGS. 6, 7 and B are a sequence of views that show an active wire excavating a tunnel in a lesion, FIG. 9 is a diagram of an acoustic signal over time, showing the response of an active wire to encountering a calcium sample representing a lesion:

FIG. 10 is a block diagram of an embodiment of the invention;

FIG. 11 is a block diagram of another embodiment of the invention;

FIG. 12 shows a typical oscilloscope image of voltage and current waveforms applied to a transducer of apparatus like that shown FIG. 1;

FIG. 13 is a side view in longitudinal section of a crossing wire and catheter coupled to an activation unit, showing possible acoustic sensor locations within the activation unit;

FIG. 14 is a side view of a crossing wire and catheter coupled to an activation unit, showing possible acoustic sensor locations on the catheter;

FIG. 15 is a perspective view of a catheter containing a crossing wire, showing a possible acoustic sensor location on the catheter;

FIG. 16 is a perspective view of a crossing wire, showing a possible acoustic sensor location on the wire;

FIG. 17 is a schematic sectional view of a patient's leg, showing an acoustic sensor of the invention incorporated into an adhesive patch applied to the leg close to the site of a lesion in the patient's vasculature;

FIG. 18 corresponds to FIG. 17 but shows an acoustic sensor unit held against the leg near the lesion instead of the adhesive patch, FIG. 19 corresponds to FIG. 18 but shows the acoustic sensor in the form of a hand-held scanner being swept over the leg near the lesion;

FIG. 20 is a schematic side view of a patient's leg, showing acoustic sensors of the invention implanted under the skin of the leg;

FIG. 21 is a schematic sectional view corresponding to FIG. 19, showing one of the acoustic sensors embedded close to the site of a lesion in the patient's vasculature;

FIG. 22 shows an acoustic signal emitted, in a frequency range up to 125 kHz, when an active wire crosses a sample of chalk;

FIG. 23 corresponds to FIG. 22 but focuses on a range up to 10 kHz;

FIG. 24 shows an acoustic signal emitted, in a frequency range up to 125 kHz, when an active wire crosses a sample of BegoStone plaster;

FIG. 25 corresponds to FIG. 24 but focuses on a range up to 10 kHz;

FIG. 26 shows an acoustic signal emitted, in a frequency range up to 125 kHz, when an active wire is not crossing a sample but is instead active in water; and FIG. 27 corresponds to FIG. 26 but focuses on a range up to 10 kHz.

FIG. 1 of the drawings shows the overall configuration of a system that implements the invention and illustrates some major components of such a system. This example features a handheld ultrasonic activation unit 2 through which a flexible transmission member in the form of an endovascular waveguide or wire 4 extends, in central alignment. In this example, portions of the wire 4 extend both proximally and distally from the activation unit 2. This arrangement is advantageous for various reasons as explained in our previous patent applications but is described here to exemplify, and not to limit, the present invention. The invention can be used with benefit in conjunction with more conventional activated crossing elements that may, for example, extend only distally from an ultrasonic actuator.

The wire 4 can be inserted into a patient's vasculature and traversed to bring its distal end to the location of a lesion. Once a complex lesion is encountered that resists the wire 4 crossing it, or before, the activation unit 2 can be coupled to the wire 4 at a suitable longitudinal location. When activated, the activation unit 2 transmits ultrasonic vibrations to and along the wire 4, enhancing the ability of the wire 4 to cross the lesion through ablation and other mechanisms. The wire 4 thereby serves as a crossing wire for crossing through an occlusion in, a blood vessel and can then remain in situ to serve as a guide wire for delivering subsequent therapeutic devices to treat the lesion.

Typically, the wire 4 may be more than 2 m and up to 3 m in length. For example, access to a lesion in or through the foot may involve the wire travelling a distance of typically 1200 mm to 2000 mm within the vasculature depending on whether an ipsilateral, contralateral or radial approach is chosen. In this respect, a wire 4 tapering distally to a fine wire at its tip can navigate to the pedal arteries and around the pedal arch between the dorsal and plantar arteries. However, the invention is not limited to pedal infra-inguinal or peripheral vessels and could, for example, be used, in coronary applications, where the ability of the wire 4 to navigate to and to excavate within tortuous small-diameter arteries is also beneficial.

The activation unit 2 may include user controls 6 and optionally also a display. The activation unit 2 further comprises a distal hand toggle 8 that a user can turn about the central longitudinal axis of the unit 2 and of the wire 4. In particular, the activation unit 2 can slide over the wire 4 and can be coupled to the wire 4 at a plurality of longitudinally spaced locations by applying torque to turn the toggle 8.

To effect coupling, as will be shown in a later drawing, the toggle 8 acts on a collet within the activation unit 2 that surrounds and is coaxial with the wire 4. When the toggle 8 is tightened, the collet grips the wire 4 to transmit ultrasonic energy from an integrated ultrasonic transducer within the activation unit 2, optionally via an amplifier horn that is coupled to the transducer. The wire 4 could be coupled directly to the transducer in some embodiments, in which case the horn may be omitted.

Rotation of the toggle 8 is reversible to release the activation unit 2 from the wire 4. Provision is thereby made to interchange wires 4 of different dimensions, configurations or materials for different purposes. There is also the possibility of interchanging the transducer, the horn and/or the collet within the activation unit 2.

In the disaggregated arrangement exemplified in FIG. 1, an ultrasonic signal generator 10 is separate from the activation unit 2 and connected to the activation unit 2 by a connector cable 12. Integrated arrangements are also possible in which the ultrasonic signal generator 10 is incorporated into the housing of the activation unit 2.

The example shown in FIG. 1 has an externally-powered ultrasonic signal generator 10 and therefore comprises a power cable 14 that connects to an external source of electrical power. Other examples may be powered by internal batteries, which may be incorporated into the ultrasonic signal generator unit 10 or into the activation unit 2.

In general, the components of the system are preferably portable and are more preferably hand-held. The components may be wireless, rechargeable, reusable and recyclable. Any external cable 12, 14 for conveying power or signals may be coupled through a slip ring to allow free rotation of the cable 12, 14 and to avoid entanglement with the wire 4.

The diameter of the distal section of the wire 4 determines the flexibility of that distal section and its ability easily to conform to the shape of the anatomy through which it is intended to pass. For example, for certain Nitinols with particular thermal transition temperatures, a distal section of an appropriate length and with a diameter of, for example, 0.005" to 0.007" combines appropriate flexibility with the ability to excavate occlusive material in a tortuous (pedal or coronary) anatomy.

When using ultrasonic energy to excite the wire 4, it is desirable to optimise displacement amplitude in and around the distal tip of the wire to excavate and cross a lesion. Conversely, it is desirable to minimise displacement or movement of the proximal end portion of the wire 4, which is outside the patient's body and part of which may hang freely from the proximal side of the activation unit 2. To achieve this, the distal length of the wire 4 from the distal tip to where the activation unit 2 is coupled to the wire 4 should be an odd multiple of a quarter wavelength of the ultrasonic wave. This creates a standing wave in the wire with a vibrating antinode at the distal tip, hence maximising the amplitude of vibration at the distal tip.

Figure 2:
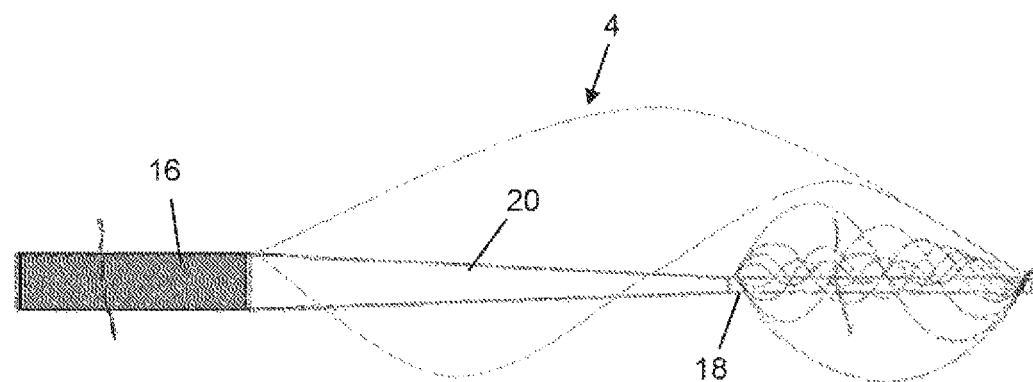
FIG. 2 is a schematic side view of a crossing wire of the apparatus, when active.

With reference now also to FIG. 2, the wire 4 includes regions where the geometry tapers to effect a change in diameter. Specifically, the wire 4 shown in FIG. 2 comprises a substantially straight proximal section 16 and a substantially straight distal tip section 18 providing an excavating part for crossing a lesion. The distal section 18 is narrower than the proximal section 16 and can be tapered or can be uniform in diameter along its length.

The distal section 18 is joined to the proximal section 16 by a distally tapering transition 20. The proximal section 16, the distal section 18 and the transition 20 are in mutual coaxial alignment along a central longitudinal axis of the wire 4, albeit substantially flexible to be bent along their length.

The purpose of the tapered transition 20 is to provide gain and to sustain the transmission of ultrasonic energy through the wire 4. For the purpose of amplification, the change in the cross-sectional area represents a level of gain in both lateral and longitudinal displacement amplitudes in the wire 4. The length and the diameter of the distal section 18 will determine the mode and magnitude of displacement in axial and radial directions. The transition 20 will also affect how a lateral mode of displacement may be established in the distal section 18 of the wire.

As with all endovascular wires, a balance is required between flexibility expressed as 'trackability' and rigidity expressed as 'pushability' or 'steerability'. As noted previously, pushability requires longitudinal, columnar stiffness whereas steerability requires torsional stiffness. However, unlike passive wires, the wire 4 must also be able to transmit ultrasonic energy to the distal section 18 to assist in crossing lesions. In this way, the wire 4 functions as an excavator, not just at its tip but also along part of its length. In particular, the distal section 18 acts radially as a lateral excavation device for opening an aperture in a lesion within a blood vessel. The wire 4 may also have distal portions shaped to amplify radial excavation.

As the goal of the activated wire 4 is to cross through a lesion, its dimensions are optimised with the purpose of excavating as large an aperture as possible for a given input. Specifically, the distal section 18 of the wire 4, once activated with ultrasonic energy as shown in FIG. 2, moves in a primary longitudinal mode, moving in and out, and also in a radial direction that maps out and excavates a greater volume at the distal end through lateral movement or radial displacement along the wire 4, The distal section 18 of the wire 4 is also seen to move through lateral and undulating movements at or near the drive frequency under the resonant wave and secondary modes of differential harmonics, dependent on the activating frequency, the length of the distal section 18 and the tortuosity of the anatomy. These waveforms may interfere with each other and be more or less effective in excavating material at different moments.

Figure 3A:
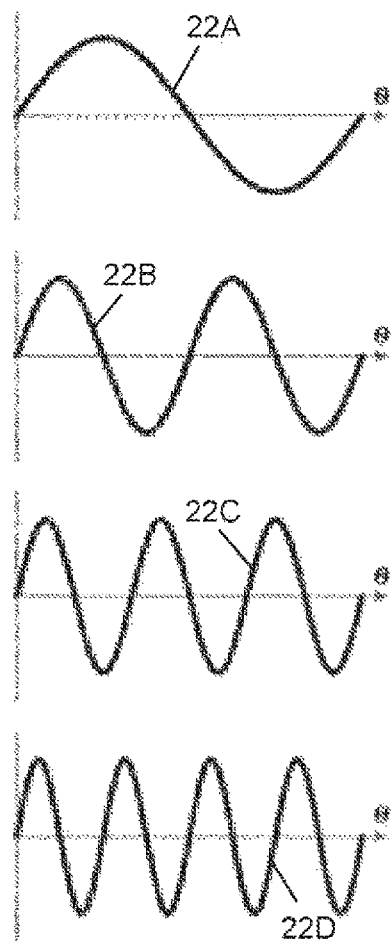
FIG. 3a represents first, second, third and fourth harmonic waveforms, the wavelength of the second, third and fourth waveforms being half that of the preceding waveform.
Figure 3B:
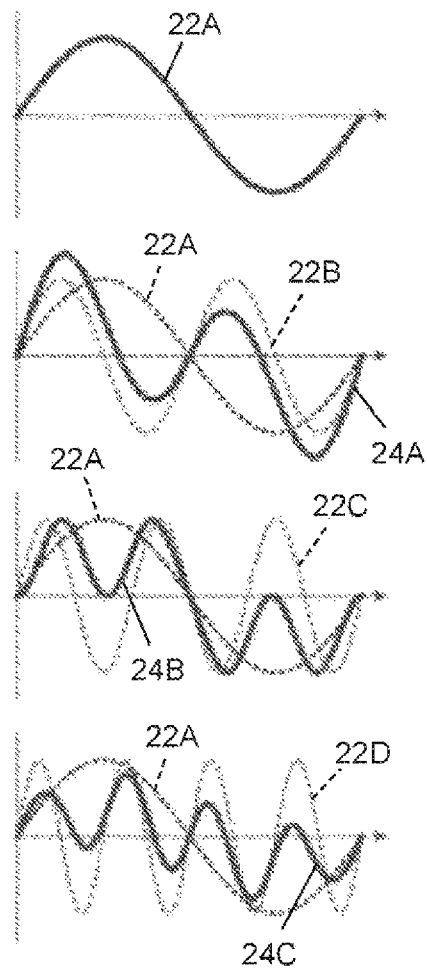
Figure 4:
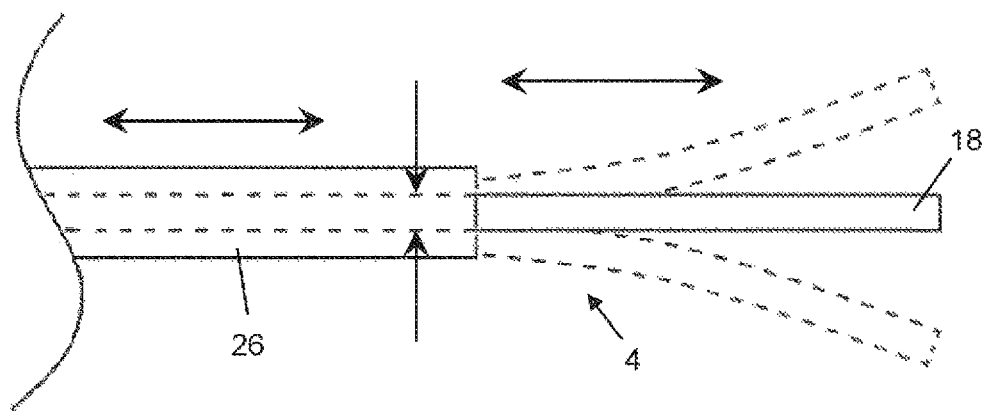
FIG. 4 is a detail side view of an active wire of the apparatus protruding distally from a catheter.

FIGS. 3a and 3b illustrate one of the reasons for these complex movements of the distal section 18 when the wire 4 is activated, FIG. 3a represents first, second, third and fourth harmonic waveforms 22A, 22B, 220 and 220. It will be noted that the wavelength of the each of the second, third and fourth subharmonic waveforms 22B, 220 and 22D is half that of the preceding waveform. FIG. 3b represents complex waveforms 24A, 248, 240 generated from combinations or superpositions of the subharmonic waveforms 22B, 220 and 22D with the harmonic waveform 22A of FIG. 3a.

Where the distal section 18 of the wire 4 emerges from a surrounding sheath or catheter 26 as shown in FIG. 4 of the drawings, additional lower-frequency lateral vibrations may arise. Freedom of movement enables the lateral component to be expressed and some component of movement may arise from a cantilever effect. In this respect, FIG. 4 shows how sleeving the wire 4 in this way leaves a desired distal length free to oscillate laterally as shown. The distal extent of sleeving, and hence the length of the free end of the wire 4, controls excavation by the distal section 18 of the wire 4. Sleeving or jacketing the wire 4 up to a resonant or harmonic length, so that the distal end of the catheter 26 substantially coincides with a resonant or harmonic length, allows the wire 4 to excavate a larger aperture.

Optionally, the catheter 26 and/or the wire 4 can be moved longitudinally relative to each other in distal and proximal directions as shown, for example by turning a thumbwheel on the activation unit 2 that acts on an outer sleeve of the catheter 26. The behaviour of the wire 4 can also be influenced by adjusting radial clearance between the catheter 26 and the wire 4 or by applying radially inward force from the catheter 26 around the wire 4 as also shown schematically in FIG. 4. Squeezing or forceful radial constraint of the wire using a collar such as a balloon has a variable effect depending on the frequency at the time as well as the relative location of the acoustic source and where it is coupled to the wire.

The diameters of the various sections 16, 18, 20 of the wire 4 are chosen for an optimal balance between pushability and trackability, in addition to being able to allow follow-on devices of standard dimensions to use the wire 4 as a guidewire. By way of example, the proximal section 16 may have a diameter of 0.43 mm and the distal section 18 may have a diameter of 0.18 mm or 0.25 mm. The taper in the intermediate transition 20 is slight and so is greatly exaggerated in FIG. 2. The transition 20 may extend over a multiple of $\lambda$ in length or a fraction of $\lambda$ in length, that fraction preferably having with a numerator of 1 and an even denominator—for example in the sequence ½, ¼, ⅛ . . . —whereas the distal section 18 may have a length of $\lambda/2$ or a multiple of $\lambda/2$ or a fraction of $\lambda/2$ such as $\lambda/4$. The optimal lengths we have found for the materials being considered for the sections 18 and 20 are $\lambda$, $\lambda/2$ and potentially $\lambda/4$ at lower sub harmonics and for fine wires.

The overall geometry of the wire 4 including its nominal diameter and length and the driving frequency of the system are determined by the characteristic speed of sound in the material of the wire. This characteristic is a function of the properties of that material and its geometry. The chosen frequency will produce harmonics along the length of the wire and the loading of the tip of the wire 4 will assist in establishing standing waves. The system may produce lateral and longitudinal displacements over a range of frequencies away from that of the drive frequency, often occurring at sub-harmonics of the frequency in the distal section 18.

In one example, which does not preclude other dimensions, a wire 4 with a core cross section diameter of 0.43 mm defining the proximal section 16 has a tapered transition section 20 optimally located to transition to a distal section 18 of 0.18 mm in diameter. The lengths of each section 16, 18, 20 of the wire 4 can be chosen to have a longitudinal resonant mode at or near the driving frequency, such as 40 kHz, with strong sub-harmonics at or near 20 kHz, 10 kHz or others. Through appropriate design, there are neighbouring lateral modes near 40 khz and 20 khz or others. There may be amplification across the tapered transition 20 by a factor of approximately 2.4 or other suitable value.

As a result, through appropriate selection of material, geometry and distal design features, desirable lateral modes will be energised as shown in FIG. 2 even when the wire 4 is driven with longitudinal vibrations. In unison, both the longitudinal and lateral vibrations contribute to excavation of a lesion and result in the wire 4 opening an aperture or lumen in the lesion whose internal diameter is substantially greater than the diameter of the wire 4.

Thus, when activated, the wire 4 serves as an excavation tool that tunnels its way by excavating material distal to the tip 18 of the wire 4 by virtue of longitudinal movement of the wire 4 and then through the offset translation or lateral motion of the wire 4 within the vasculature, which provides a lateral offset that opens up the diameter of the tunnel.

Consequently, the wire 4 abrades the inner surface of the occlusion not just at its distal tip but also along some of its length extending proximally from the distal tip and forms a wider aperture for the passage of follow-on therapeutic devices over the wire 4. This effect is shown in FIGS. 5 to 8 of the drawings.

Figure 5:
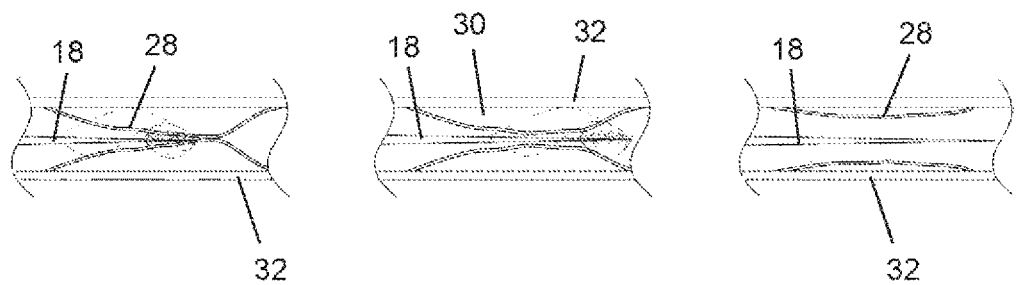
FIG. 5 is a series of drawings showing the wire when active, excavating a tunnel in a lesion that was blocking a blood vessel.

FIG. 5 shows how the distal section 18 of the wire 4 may excavate an aperture 28 in the lesion 30 whose diameter is greater than the diameter of the wire 4 and so create a larger lumen through which therapies may be introduced to the lesion 30. The active wire 4 performs both longitudinal, axial or directional excavation as well as radial; lateral or orbital excavation through orbiting of the wire 4 out of the axial plane of the wire 4 at different harmonics in a consistent, monotonic manner.

The wire 4 can be navigated along a vessel 32 to the lesion 30 in an active or passive mode. Once activated and brought into contact with the lesion 30, the wire 4 moves from a 'fixed to free' state to a 'fixed to fixed' state, which to some extent attenuates the expressed amplitude in the wire 4. As the wire 4 passes through the lesion 30, subharmonic displacements are expressed and then as the wire 4 returns to a 'fixed to free' state, lateral subharmonic components are expressed to excavate the larger aperture 28. Thus, lateral oscillation of the wire 4 carves out a channel through the lesion 30 in the lumen of the vessel 32.

Figure 8:
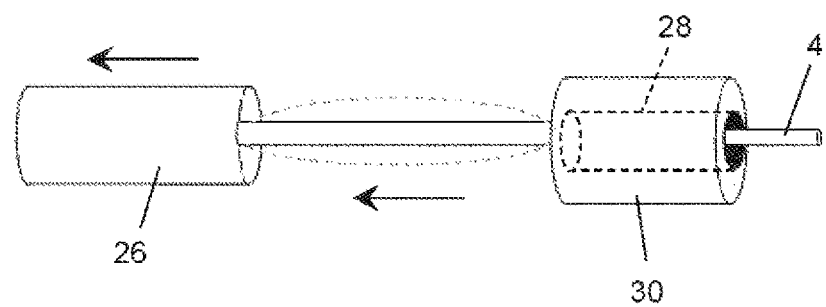

FIGS. 6, 7 and 8 exemplify how the ability to alter the relative longitudinal position of the wire 4 and the catheter 26 can be exploited to affect the lateral motion of the distal end of the wire 4, thereby influencing secondary or lateral excavation, burrowing or tunnelling of the lesion 30 by the wire 4 within the lesion 30. In particular. FIGS. 6, 7 and 8 show, schematically, how the distal end of the wire 4 firstly penetrates the lesion as shown in FIG. 6, to create a longitudinal aperture 28 and then, with lateral oscillation of the wire 4 optimised, widens the aperture 28 to create a lumen of the desired diameter as shown in FIGS. 7 and 8.

When a sufficient free end length of the wire 4 extends distally beyond the lesion 30, lateral oscillation in that free end portion begins lateral excavation of the distal segment of the lesion 30 as shown in FIG. 7. Then, drawing the activated wire 4 back proximally through the lesion 30 extends and widens the aperture 28 as shown in FIG. 8, aided by lateral oscillation being optimised in the portion of the wire 4 between the catheter 26 and the lesion 30. If required, the activated wire 4 can then be pushed distally back through the lesion 30 to widen the aperture 28 further.

Referring back to FIGS. 2 to 8, it will be apparent that the behaviour of the active wire 4, and particularly its distal tip section 18, will change as the wire 4 is influenced by its changing surroundings in use within the anatomy. Thus, the behaviour of the wire 4 will depend upon the position of the distal tip section 18 in the anatomy, the medium in which the distal tip section 18 moves, and especially the materials and structures with which the distal tip section 18 comes into contact. These behaviours, and changes between them, will be expressed in terms of wavelength, frequency, amplitude and the expression of subharmonic and complex waveforms.

The invention embodies a principle, which is that these characteristics of the behaviour of an active wire 4 produce distinctive acoustic emissions that can be detected and analysed to determine that behaviour and thereby to infer the factors that produce that behaviour. Thus, it is possible to use an acoustic signature to infer information such as the medium in which the distal tip section 18 is moving and the materials and structures with which the distal tip section 18 is, in contact.

To illustrate this principle, FIG. 9 shows an acoustic signature of an active wire 4 before contact with a lesion 30, on the left, and during contact with a lesion 30, on the right. Two acoustic signatures are shown on the right of FIG. 9: one from an acoustic sensor positioned distally, close to the active tip of the wire 4 and the other from an acoustic sensor positioned proximally, for example in or adjacent to an activation unit 2. The acoustic signature is plotted as frequency on the vertical axis against time on the horizontal axis. In this example, the lesion 30 was represented by a sample of calcium carbonate in the form of chalk. The wire 4 was driven at a frequency of 40 kHz.

It will be apparent that before contact with the lesion 30, as shown on the left of FIG. 9, the wire 4 predominantly expresses vibrations around the sub-harmonic of 20 kHz. Conversely, during contact with the lesion 30 as shown on the right of FIG. 9, the wire 4 begins to express vibrations at various subharmonic frequencies below 20 kHz, as marked by the ellipse A. The acoustic signature therefore reflects that the wire 4 is now in the process of crossing through the lesion 30. Moreover, aspects of the acoustic signature, when analysed and compared with known signatures, can characterise the lesion 30 itself. For example, the onset of cavitation is typically marked by an increase in broadband noise.

FIG. 10 illustrates the components and elements of a system 34 for detecting and acting on acoustic feedback from the active wire 4. FIG. 10 also shows the flow of data through the system, including communications. A controller 36, which may be in the housing of the activation unit 2, controls an ultrasonic generator 38 to generate a signal that is converted to ultrasonic energy by a transducer 40. The ultrasonic energy is fed via a coupling 42 such as the aforementioned collet and an optional acoustic horn to the active wire 4 that navigates the vasculature, and crosses a blockage such as a CTO.

Acoustic feedback from the active wire 4 is received by one or more acoustic sensors 44 such as microphones or other transducers, amplified by an amplifier 46 and filtered by a series of bandpass filters 48 before undergoing analog-to-digital conversion 50 to generate feedback data that is sent to a processor 52. The controller 36 controls a preferably wireless communications system 54, for example using a Wi-Fi network or a Bluetooth connection, to receive data from the processor 52 and to communicate that data from the housing unit to local storage 56 and/or to the cloud 58. FIG. 4 also shows a means for providing feedback to a user; such as the aforementioned display and/or a haptic feedback system.

The system 62 shown in FIG. 11 is a refinement of the system 34 of FIG. 10. Like numerals are used for like features. In the system 62 of FIG. 11, non-acoustic feedback is obtained from a second, additional source, namely a feedback receiver 64. Signals from the feedback receiver 64 are amplified by an amplifier 46 and filtered by bandpass filters 48 before undergoing analog-to-digital conversion 50 to generate additional, auxiliary feedback data that is sent to the processor 52.

The feedback receiver 64 may, for example, detect changes in impedance in the transducer 40 that drives the wire 4, those changes being attributed to changing losses in the system as the wire 4 is damped or becomes more or less constrained. For example, increased damping lowers the Q factor of the system.

Q factor can be measured as shown in FIG. 12. The upper trace in FIG. 12 shows voltage applied by the ultrasonic generator 38 to the transducer 40. The lower trace shows current through the transducer, as measured by the feedback receiver 64. When the voltage signal is stopped abruptly, the system continues to resonate for a length of time proportional to Q. By curve-fitting an exponential decay function to the current signal, the processor 52 may derive a value for and hence damping. This value is influenced by the nature of the lesion 30.

Characterisation of impedance changes may involve separating out differences based on location or dynamic variations and comparison of variations in voltage, current and phase angle between different times. Superimposition of data representing this electrical response with data representing the corresponding acoustic response at a given point in time can be used to analyse and describe the characteristics of a vessel 32, its lumen and any lesion 30 more accurately.

Similarly, it would be possible to employ two or more acoustic sensors 44 at different positions in the system or relative to a lesion 30 to provide additional acoustic data to corroborate and confirm the measured characteristics of a vessel 32, its lumen and any lesion 30. FIGS. 12 to 20 show various possibilities in this respect, it being understood that one, two or more acoustic sensors 44 could be employed at or near any of the positions described and illustrated.

In general, acoustic sensors 44 can be placed at any of various positions in the system. Different sensor positions will produce different acoustic signatures. Locating multiple acoustic sensors around the transducer 40 and an associated collet can produce different relative patterns of characteristic spectra that can be subject to interrogation for association with different features. An external acoustic sensor could also integrate lighting such as an LED to provide visual feedback in respect of the performance of the system. This could be interpolated from changes in the acoustic signature or an overlay of the acoustic response over the electronic or electrical response of the system.

Turning next, then, to FIG. 13, this shows an ultrasonic activation unit 2 through which a wire 4 extends longitudinally. In this example, the activation unit 2 is powered externally and is optionally supplied with an ultrasonic signal through a cable 12.

FIG. 13 shows that the activation unit 2 contains an ultrasonic transducer 40 and a distally tapering acoustic horn 66 attached to the distal face of the transducer 40. A collet 68 couples the wire 4 to the distal end of the horn 66. The transducer 40, the horn 66 and the collet 68 are penetrated by a central lumen to allow for the through-passage of the wire 4. The wire 4 thereby extends though the full length of the activation unit 2 to emerge proximally from the activation unit 2. The activation unit 2 can be moved along the wire 4 and then can be coupled to transmit ultrasonic energy to the wire 4 at any of a various locations along the wire 4. In other arrangements, the wire 4 could instead emerge from the activation unit 2 laterally at a proximal location with respect to the collet 68.

In FIG. 13, the catheter 26 that surrounds and supports the wire 4 can be coupled to a distal region of the wire 4. In this, example, coupling is effected by a distal annular balloon 70 within the catheter 26, which expands into the distal inner lumen of the catheter 26 around the wire 4. The balloon 36 may be inflated via an inflation port 38 on the catheter 26. Additional ports and lumens may be included in the catheter 26, for example to provide for aspiration of embolus or of fragments or particles generated during excavation.

Optionally, the balloon 70 or other coupling may be configured to grip the wire 4, applying inward clamping force to the distal portion of the wire 4. In this way, ultrasonic energy could be coupled through waveguide elements of the catheter 26, transmitting electromechanical energy from the catheter 26 through to the distal tip region of the wire 4 via the coupling through the balloon 70.

The proximal end of the catheter 26 is coupled to the transducer 40 by an adapter element 72. The proximal end of the adapter element 72 abuts the distal end of the horn 66 around the collet 68 and is thereby coupled to the transducer 40 to receive ultrasonic energy. In principle, the adapter element 72 can facilitate transmission of energy from the transducer 40 in any of three modes of operation, namely: the wire 4 being activated independently; the catheter 26 being activated independently: or the catheter 26 and the wire 4 being activated simultaneously.

Acoustic sensors 44 may be placed on the outside of the activation unit 2, in the body of the activation unit 2 or on different sections of the catheter 26. Differential placement of acoustic sensors can provide for distinctive interference and characteristic patterns in the acoustic spectra.

In the example shown in FIG. 13, acoustic sensors 44 are disposed on the adapter element 72 adjacent to the collet 68 and proximally relative to the collet 68, here being mounted on the housing of the activation unit 2.

In addition to locating an acoustic sensor 44 in the housing or casing of the activation unit 2, an option would be to house the acoustic sensor 44 outside the housing, for example along a catheter 26. In this respect. FIG. 14 shows the exterior of an activation unit 2 with a catheter 26 extending distally from the unit 2. Here, various acoustic sensors 44 are disposed distally relative to the collet 68. One acoustic sensor 44 is positioned at the distal end of the unit 2, specifically on or in the toggle 8 that acts on the collet 68 within. Two more acoustic sensors 44 are shown on the catheter 26, one near the proximal end and the other near the distal end of the catheter 26, FIG. 15 shows a catheter 26 and the wire 4 within, separately from the activation unit 2. An acoustic sensor 44 is shown near the distal end of the catheter 26. Thus, the catheter 26 provides a means to introduce an acoustic sensor intravascularly.

Incorporation of an acoustic sensor 44 in a catheter 26 and its introduction over a wire 4 to the location of a blockage or the distal end of the wire 4 provides a way of measuring the manner of the interaction between the wire 4, the blood and any acoustic effects created by the interaction between the wire 4 and the vessel 32 or any blockage 30 within it. As noted previously, it is possible to adjust and control the distance by which the wire 4 extends beyond a microcatheter sleeve, hence the length of wire 4 that is exposed into the lumen of the vessel 32. This adds additional control over how the wire 4 is excited and how acoustic emissions may be created from within the vessel 32.

Housing the acoustic sensor 44 in or on the catheter 26 makes the entire system more efficient. The proximity of the wire 4 to the acoustic sensor 44 and the ability to capture emissions from the catheter 26 increase the reliability of acoustic sensing and reduce variability that might otherwise arise from variations in the tissues while being more sensitive to the variations that might arise in the patterns of acoustic emissions that would arise from interaction between the wire 4 and the catheter 26.

FIG. 16 shows that a sensor could even be applied to the wire 4 itself, for example in the form of an electrical or optical strain gauge 74, in this example, the strain gauge is affixed to the proximal section 16 of the wire 4, close to the tapered transition 20 that leads to the thinner distal section 18 of the wire 4. Such a sensor could serve as an acoustic sensor or could more directly determine the behaviour of the wire 4 from strains experienced by the wire 4 when activated. For example, integrating an acoustic emitter or a micro array on the surface of the wire 4 can provide a means to optimise the emissions in specific ranges of interest. Signals from the strain gauge 74 could further corroborate data received from acoustic sensors 44, in addition to or instead of non-acoustic feedback from a feedback receiver 64 such as that shown in FIG. 11.

FIGS. 17 to 21 show various ways of positioning acoustic sensors on or in a patient's body, exemplified here by the patient's leg 76, In each case, an active wire 4 has been advanced through the patient's vasculature and into a vessel 32 blocked by a lesion 30, shown here in the lower leg 76. The distal tip of the wire 4 has engaged the lesion 30 and is about to be activated with ultrasonic energy to begin excavating a channel through the lesion 30.

FIGS. 16 to 19 show extra-corporeal positioning of acoustic sensors 44. Positioning acoustic sensors 44 externally of the body allows for the interrogation of acoustic emissions from the wire 4 and the vessel 32 through the surrounding tissues.

In FIG. 16, the acoustic sensor 44 is integrated into a surgical patch or embodied in a surgical band or the like to bring the acoustic sensor 44 into close proximity to the tissue. The acoustic sensor 44 is located close to the area of interest, be that along the length of the vessel 32 or otherwise in a region of the patient's body affected by the disease of the vessel 32. Alternatively, an ultrasonic probe could serve as an acoustic sensor 44 to detect acoustic emissions as shown in FIG. 17 as a stationary unit and in FIG. 18 as a hand-held unit that can be swept over the patient's skin close to the lesion 30. The data from the probe can then be used directly to interpolate the location and proximity to the lesion 30 and the manner in which movement of the wire is disturbed, characterising whatever blockages may be present.

FIGS. 20 and 21 show intra-corporeal positioning of acoustic sensors 44 on probes 78 positioned internally of the body. This allows the acoustic sensors 44 to be introduced through the tissues into the compartment surrounding the vessel 32, getting closer to the region of the vessel 32 where the lesion 30 is being treated or the region of the vessel 32 to be assessed for diseased medial tissue.

Surgical insertion into the tissue of a probe 78 carrying an acoustic sensor 44 at its distal tip provides a way of getting closer to the region of the lesion 30 or the vessel 32. This enables detection of acoustic emissions from the interaction between the wire 4 and its surroundings and its transmission through the vessel 32, without losses and aberrations to the acoustic spectra that could arise from passage through a significant thickness of muscle and skin.

Finally, FIGS. 22 to 27 show acoustic signals emitted, and especially how specific frequencies are expressed, as an active wire crosses through different materials. The materials chosen were chalk (FIGS. 22 and 23), BegoStone (FIGS. 24 and 25) and water (FIGS. 26 and 27). BegoStone (registered trade mark) is a commercially available super-hard plaster originally developed for dental applications. In each case, the signals were obtained with the wire and samples in a bath of water, using a hydrophone positioned near the distal tip of the wire. The signals were captured on an oscilloscope and were not post-processed.

For each material, the acoustic signal is shown across a wide frequency range of up to 125 kHz (in FIGS. 22, 24 and 26) and in a narrower low (audible) resonance range of up to 10 kHz (in FIGS. 23, 25 and 27). The lower range is taken from the larger data set, itself, a sample in time.

Nominally, the system is designed to drive at 40 kHz but with the wire 4 and collet 68 in place, the system actually resonates at (and therefore the electronics drive the system at) a slightly different frequency of about 38 kHz. Consequently, if all other acoustic influences were subtracted, it would be expected only to see a line at a frequency of around 38 kHz. Such a line is evident and can also be measured electronically by the feedback receiver 64, as is a line at 40 kHz at which the wire 4 is designed to resonate. However, several additional emitted resonant frequencies are observed as features appearing at different frequencies, notably at the harmonics of the drive frequency of the system, but also at others. Thus, in addition to the line at 38 kHz, high amplitudes of acoustic emissions can be seen at the harmonics 8 kHz, 19 kHz and 76 kHz and at even higher frequencies such as 114 kHz. Other characteristic features establish themselves around and between these harmonics of the drive frequency. In the lower range shown in FIGS. 23, 25 and 27, characteristic emissions are also expressed at different frequencies.

Many other variations are possible within the inventive concept. For example, one or more acoustic sensors 44 could be disposed on a distal tube like those disclosed in our previous patent application published as WO 2021/224357. Such tubes extend distally from the activation unit 2 to protect and guide the wire 4 within, to provide strain relief and/or to apply damping force to the wire 4. They may also serve as a connector to a structure disposed distally of the activation unit 2, such as a luer fitting or other entry port.

In another variation, it is possible deliberately to change the nature of the stimulus signal applied to the transducer 40. In the general case (and as shown in FIGS. 21 to 26) the stimulus applied is a continuous sine wave of one frequency. However, the use of other waveforms, such as pulsed, multi-tone, chirp or noise waveforms, allows different characteristics to be extracted from the corresponding response signals. This exploits the ability of the processor 52 to correlate the input stimulus with the output responses.

To maximise the sensitivity of the system when analysing response signals from the feedback receiver 64 and/or acoustic sensors 44, it is possible to create a 'baseline' response signal that may be subtracted later from the changing response signals. The baseline is most usefully obtained when the distal tip of the wire 4 is close to a lesion 30 but not touching it. In this way, the baseline response signals encapsulate all of the underlying characteristics of the system, including the tortuosity of the vasculature through which the wire 4 extends to the lesion 30. Alternatively, the baseline may be obtained automatically, on a continuous basis, and the system itself can decide when to apply a subtraction algorithm.

The invention claimed is:

1. Endovascular apparatus for determining the condition of a vessel in a body, the apparatus comprising:
   an elongate waveguide element, being a wire;
   an activation unit comprising a source of ultrasonic energy and a coupling for coupling the source to the wire to activate the wire, thereby transmitting ultrasonic energy from the source along the wire to an active distal section of the wire; and
   a signal acquisition system that is configured to acquire feedback signals from the apparatus for interpretation of vessel condition;
   wherein the signal acquisition system comprises at least one acoustic sensor for acquiring acoustic feedback signals generated by interaction of the active distal section of the wire with neighbouring tissues or obstructions when the wire is activated, the at least one acoustic sensor being outside a housing of the activation unit, the at least one acoustic sensor further being:
- an extra-corporeal sensor arranged to lie against a part of the body, or
- an intra-corporeal sensor arranged to be inserted into the body, or
- mounted on a catheter surrounding the wire.

2. The apparatus of claim 1, wherein at least one acoustic sensor is mounted in or on the activation unit.

3. The apparatus of claim 2, wherein at least one acoustic sensor is mounted in longitudinal alignment with, or proximally relative to, the coupling of the activation unit.

4. The apparatus of claim 2, wherein at least one acoustic sensor is mounted distally relative to the coupling of the activation unit.

5. The apparatus of claim 1, wherein at least one acoustic sensor is mounted parallel with the wire.

6. The apparatus of claim 1, wherein a strain gauge is fixed to the wire to acquire operational feedback signals from the wire.

7. The apparatus of claim 6, wherein the strain gauge serves as an acoustic sensor.

8. The apparatus of claim 1, wherein the signal acquisition system comprises at least two acoustic sensors longitudinally spaced from each other.

9. The apparatus of claim 1, wherein the signal acquisition system further comprises at least one electronic sensor that is configured to acquire operational feedback signals representing operational parameters of the source of ultrasonic energy.

10. The apparatus of claim 9, wherein the operational parameters are frequency and/or amplitude and/or phase of current drawn by, or voltage dropped across, the source of ultrasonic energy.

11. The apparatus of claim 1, wherein the signal acquisition system is configured to monitor variations in frequency or amplitude of vibration of the wire via the coupling.

12. The apparatus of claim 1, further comprising a signal processing system for processing feedback signals acquired by the signal acquisition system.

13. The apparatus of claim 12, wherein the signal processing system is configured to employ numerical algorithms selected for specific types of wire.

14. The apparatus of claim 12, wherein the signal processing system is configured to determine characteristics of an obstruction in a vessel from the acquired feedback signals.

15. The apparatus of claim 12, wherein the signal processing system is configured to compare relative contributions of losses from anatomical tortuosity in navigating the active distal section to an obstruction versus losses arising from the passage of the active distal section through the obstruction.

16. The apparatus of claim 12, wherein the signal processing system is configured to compare the acquired feedback signals with stored data that characterises known obstructions, and to characterise an obstruction with reference to that comparison.

17. The apparatus of claim 12, wherein the signal processing system further comprises an output to a user interface and/or to an external data acquisition system.

18. The apparatus of claim 12, wherein the signal processing system further comprises an input from a user interface and/or from an external data network.

19. The apparatus of claim 12, further comprising a controller that is responsive to the signal processing system.

20. The apparatus of claim 19, wherein the controller is configured to modulate excitation voltage applied to, or excitation current supplied to, the source of ultrasonic energy.

21. The apparatus of claim 20, wherein the controller is configured to control the source of ultrasonic energy by varying frequency and/or amplitude of the excitation voltage applied to the source of ultrasonic energy.

22. The apparatus of claim 20, wherein the controller is configured to drive the frequency of the excitation voltage by employing a phase difference between the excitation voltage and the excitation current in conjunction with amplitude of the excitation voltage.

23. The apparatus of claim 19, wherein the controller comprises an amplitude feedback controller and is configured to use a resonant frequency as an operating point of control.

24. The apparatus of claim 19, wherein the controller is configured to pulse or vary a drive signal to the source of ultrasonic energy.

25. The apparatus of claim 19, wherein the controller is configured:
- to monitor modulation of transmitted signals and to control the source of ultrasonic energy automatically to compensate for background energy loss encountered in the wire as the active distal section approaches an obstruction; and
- to distinguish the background energy loss from additional energy loss as the active distal section passes through the obstruction and to compensate for the background energy loss to sustain displacement at the active distal section.

26. The apparatus of claim 19, wherein the controller is configured to modify or change a control algorithm in response to variation in operational parameters of the source of ultrasonic energy arising from interaction of the active distal section with an obstruction in use.

27. A communication system comprising the apparatus of claim 1 in data communication with a computer system that is arranged to receive data from the apparatus, to optimise and update control algorithms accordingly and to output the optimised, updated control algorithms to the apparatus.

28. The communication system of claim 27, wherein two or more such apparatuses are in data communication with the computer system, which is arranged to optimise control algorithms in accordance with data received from multiple procedures performed using the apparatuses and to output the optimised, updated control algorithms to the apparatuses.

* * * * *